(12) United States Patent
Fukuma et al.

(10) Patent No.: US 7,370,966 B2
(45) Date of Patent: May 13, 2008

(54) OPTHALMOLOGIC APPARATUS

(75) Inventors: Yasufumi Fukuma, Tokyo (JP); Hiroyuki Otsuka, Tokyo (JP); Kazuhiko Yumikake, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/697,042

(22) Filed: Apr. 5, 2007

(65) Prior Publication Data

US 2007/0236661 A1 Oct. 11, 2007

(30) Foreign Application Priority Data

Apr. 7, 2006 (JP) ............................. 2006-106936

(51) Int. Cl.
*A61B 3/10* (2006.01)
*A61B 3/14* (2006.01)

(52) U.S. Cl. ...................... 351/205; 351/208; 351/214; 351/221

(58) Field of Classification Search ................ 351/200, 351/204–206, 208, 210, 214, 221
See application file for complete search history.

(56) References Cited

U.S. PATENT DOCUMENTS 5,329,321 A * 7/1994 Koizumi ..................... 351/205

FOREIGN PATENT DOCUMENTS

| JP | 05-277075 | 10/1993 |
|---|---|---|
| JP | 2001-061784 | 3/2001 |
| JP | 2003-000543 | 1/2003 |
| JP | 2004-350849 | 12/2004 |
| JP | 2005-241464 | 9/2005 |

* cited by examiner

*Primary Examiner*—Huy Mai
*Assistant Examiner*—Jack Dinh
(74) *Attorney, Agent, or Firm*—Frost Brown Todd LLC

(57) ABSTRACT

The ophthalmologic apparatus 1 splits low coherence light LO into a signal light LS and a reference light LR, the interference light LC being generated by having the signal light LS overlap with the reference light LR, and detects this interference light LC. In addition, the apparatus comprises an optical alignment system 190A for performing the alignment of an optical system forming the signal light path to the eye E. An intraocular distance calculator 214 determines the distance between the position where the signal light LS has been introduced onto the eye E and the position where the signal light LS has been reflected by the fundus oculi E based on length of the optical path of the signal light, the length of the optical path of the reference signal light, the working distance after alignment, and the detection signal output by the CCD 184 (or signal intensity data).

4 Claims, 15 Drawing Sheets

OPTHALMOLOGIC APPARATUS

BACKGROUND OF THE INVENTION

1. Field of the Invention

The present invention relates to an ophthalmologic apparatus capable of measuring distance in the oculus of an eye.

2. Description of the Related Art

For an ophthalmologic apparatus for measuring distance in the oculus of an eye (e.g., axial length), a method of utilizing ultrasonic waves and a method of utilizing light are commonly employed. A method of utilizing ultrasonic waves is disclosed, for example, in JP Patent laid-open No. 2001-61784. In addition, the method of utilizing light is disclosed in JP Patent laid-open No. Hei 5-277075.

Methods of utilizing ultrasonic waves are problematic in that they impose mental and physical strain on the subject during measurement by bringing an ultrasonic probe into contact with the cornea of the eye (more specifically, by indirect contact via liquid or gel ultrasonic waves medium). Moreover, since the eye needs to be disinfected prior to measurement, it is problematic in that the work takes time or imposes strain on the subject. On the other hand, methods of utilizing light have an advantage in that strain on the subject is smaller than in the case of ultrasonic waves and work such as disinfecting is not required since measurement is possible without contact with the eye.

Herein, as an example of the ophthalmologic apparatus according to the present invention, the related art of an apparatus is described in "Preferred Embodiment of the Invention". This apparatus is comprised of a fundus camera and an OCT (Optical Coherence Tomography) technology applied apparatus (referred to as optical image measuring device, light coherence tomography apparatus, and so on.).

FIG. 14 shows one example of the appearance of a conventional fundus camera in general, and FIG. 15 shows one example of an optical system composition to be internally accommodated therein (e.g. JP Patent laid-open No. 2004-350849). This fundus camera 1000 is provided with a platform 3 mounted on a base 2 slidably in the front and rear, right and left (horizontal direction) directions. On this platform 3, an operation panel 3a and a control lever 4 are installed for an examiner to conduct various operations.

The examiner may place the platform 3 on the base 2 to be moved 3-dimensionally by operating the control lever 4. On the top of the control lever 4, an operation button 4a is installed to be pressed down to obtain fundus oculi images.

On the base 2, a post 5 is installed standing upwards. On the post 5, a jaw rest 6 where the jaw of a patient is to be rested and an external fixation lamp 7 as a light source for fixing an eye E are provided.

On the platform 3, a main body part 8 is installed to accommodate various optical systems or control systems of the fundus camera 1000. Furthermore, the control system may be installed inside the base 2 or the platform 3, etc., or in an external device such as a computer, etc. connected to the fundus camera 1000.

On the side of the eye E of the main body part 8 (the left side of the page in FIG. 14), an objective lens part 8a disposed opposite the eye E is installed. Also, on the examiner's side of the main body part 8 (the right side of the page in FIG. 14), an objective lens part 8b for observing the fundus oculi of the eye E with the naked is installed.

Furthermore, connected to the main body part 8 is a still camera 9 for producing a still image of a fundus oculi of the eye E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data can be sent to an image storing device connected to the fundus camera 1000 to compile a database and be used as electronic data for creating medical charts, etc.

Furthermore, on the examiner's side of the main body part 8, a touch panel monitor 11 is installed. On this touch panel monitor 11, fundus images of the eye E created based on the video signals output from the still camera 9 (a digital method thereof) or the imaging device 10 are displayed. Moreover, on the touch panel monitor 11, the 2-dimensional coordinate system with the center of the screen as the origin is displayed overlapped with a fundus image. When the screen is touched by the examiner, the coordinate value corresponding to the touched position is displayed.

Next, referring to FIG. 15, a composition of an optical system of the fundus camera 1000 is described. The fundus camera 1000 is provided with an illuminating optical system 100 to light the fundus oculi Ef of an eye E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, an imaging light source 103, a condenser lens 104, an exciter filter 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits continuous light for observing the fundus. The condenser lens 102 is an optical element that converges the continuous light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of images of a fundus oculi Ef takes a place. The exciter filters 105 and 106 respectively can be inserted and removed on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye E.

The illumination diaphragm 110 is a diaphragm member to shut out a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112 an aperture part 112a is opened. The light axis of the illuminating optical system 100 and the light axis of the imaging optical system 120 are to be crossed at a substantially central location of this aperture part 112a. The objective lens 113 is installed in the objective lens part 8a of the main body part 8.

The illuminating optical system 100 having such a composition illuminates a fundus oculi Ef in the following manner. First, the observation illumination light is emitted when the observation light source 101 is lit during fundus observation. This observation illumination light irradiates the ring transparent plate 107 through the condenser lenses 102 and 104. (The exciter filters 105 and 106 are removed from the optical path.) The light passed through the ring transparent part 107a of the ring transparent plate 107 is reflected by the mirror 108 and is reflected along the optical axial direction of the imaging optical system 120 due to the aperture mirror 112 through the LCD 109, the illumination diaphragm 110 and the relay lens 111. The observing illumination light reflected by the aperture mirror 112 advances in the optical axial direction of the imaging optical system 120 and is converged by the objective lens 113, to be made incident onto the eye E, and illuminates the fundus oculi Ef.

Then, the ring transparent plate 107 is disposed in a conjugating location with the pupil of the eye E, and on the pupil a ring shaped image of the entering observation illumination light is formed. The fundus reflection light of the entered observation illumination light is to be emitted from the eye E through a central dark part of the ring image on the pupil. As described, it is to protect the effect of observing illumination light entering the eye E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is carried out.

Imaging optical system 120 comprises: an objective lens 113, an aperture mirror 112 (an aperture part 112a thereof), an imaging diaphragm 121, a barrier filter 122 and 123, a focusing lens 124, a relay lens 125, an imaging lens 126, a quick return mirror 127 and an imaging media 9a. Herein, the imaging media 9a is an arbitrary imaging media (image pick-up elements such as CCD, camera film, instant film, etc.) used for a still camera 9.

The fundus reflection light of the illumination light, emitted through the central dark part of the ring shaped image formed on the pupil from the eye E, enters the imaging diaphragm 121 through the aperture part 112a of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism (not illustrated herein).

The barrier filters 122 and 123 can be inserted and removed on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when producing color images the barrier filters 122 and 123 are to be retracted from the optical path.

The focusing lens 124 is to be movable in the light axial direction of the imaging optical system 120 by a drive mechanism (not illustrated herein). This makes it possible to change the magnifying ratio of an observation and the magnifying ratio in imaging, and to focus images of a fundus oculi. The imaging lens 126 is a lens to focus the fundus reflection light from an eye E on the imaging media 9a.

The quick return mirror 127 is disposed rotatably around a rotary shaft 127a by a drive mechanism not illustrated herein. In the event of imaging a fundus oculi Ef with the still camera 9, the fundus reflection light is supposed to be guided to the imaging media 9a by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133 and an image pick up element 10a. The image pick up element 10a is an image pick up element such as CCD, etc. installed internally in the imaging device 10. On the touch panel monitor 11 a fundus oculi image Ef' imaged by the image pick up element 10a is be displayed.

The switching mirror 129 is to be rotatable around the rotary shaft 129a as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10a. In this case, the fundus reflection light is directed toward a relay lens 131, is reflected by the mirror 132, and is focused on the image pick-up element 10a by the imaging lens 133.

Such a fundus camera 1000 is an ophthalmologic apparatus to be used for observing the state of the surface of a fundus oculi Ef, that is, the retina. In other words, a fundus camera 1000 is a ophthalmologic apparatus to obtain a 2-dimensional fundus oculi image when it sees the fundus oculi Ef from the corneal direction onto the eye E. On the other hand, in the deep layer of retina tissues such as the choroidea or sclera exist, technology for observing these deep layer tissues has been desired, but, in recent years, devices for observing these deep layer tissues have been practically implemented (e.g. JP Patent laid-open No. 2003-000543, JP Patent laid-open No. 2005-241464).

With the optical image measuring device disclosed in JP Patent laid-open No. 2003-000543 and JP Patent laid-open No. 2005-241464, low coherence light is split into two, one of which (signal light) is guided to a fundus oculi and the other one (reference light) is guided to a given reference object, and this is a device to form tomographic images of the surface and the deep layer tissue of a fundus oculi,and to form the 3-dimensional image from the tomographic images, by detecting and analyzing the interference light obtained by overlaying the signal light that has reached the fundus oculi and the reference light that has been reflected by the reference object. Such devices disclosed in JP Patent laid-open No. 2003-000543 are in general called a Fourier domain OCT.

The Fourier domain OCT is designed to form a tomographic image having a depth-wise cross-section along its scanning line by scanning and irradiating a signal light onto the fundus oculi. Such scanning of signal lights is referred to as a B-scan (see NEDO Workshop "Seeing (examining) inside the body from the 'window' of the human body, the fundus oculi"—Development of an ultra early diagnostic device for lifestyle-related diseases using the latest optical technologies (held on Apr. 25, 2005), Internet<URL: http://www.nedo.go.jp/informations/koubo/170627_2/besshi3.pdf>).

When forming a 3-dimensional image of fundus oculi of an eye, a B-scan is performed along a plurality of scanning lines, and an interpolation process is applied to the resulting plurality of tomographic images for the generation of 3-dimensional image data. This 3-dimensional image data is referred to as volume data, voxel data, and so forth, as well as medical imaging diagnosis devices such as an X-ray CT device, which is image data in a form in which pixel data (e.g. luminance value and RGB value regarding brightness, contrasting density and color) is assigned to each voxel. A 3-dimensional image is displayed as a pseudo 3-dimensional image seen from a certain viewing angle obtained by rendering volume data.

The axial length of an eye is employed in the positioning of IOL (Intraocular Lens) inserted into the eye, for example, in cataract surgery or the like, so it requires high measurement accuracy. In the measurement of axial length using ultrasonic waves, the accuracy of measurement is lower than methods using light since the wavelength of ultrasonic waves is relatively long (measurement error greater than the wavelength of the measurement waves occurs). Therefore, it is considered that distance in the oculus such as axial length should be determined using an optical method.

The present invention is based on the circumstances described above, with the purpose of providing an ophthalmologic apparatus allowing measurement of distance in the oculus using a new optical method.

SUMMARY OF THE INVENTION

In order to achieve the above purpose, the first aspect of the present invention is constructed as follows; a light source for outputting a low coherence light, an interference light generating part for splitting the low coherence light output into the signal light directed toward the fundus oculi of an eye and the reference light directed toward the reference object, and overlapping the signal light irradiated onto the eye via a signal light path and reflected by the fundus oculi and the reference light reflected by said reference object via a reference light path, a detecting part for receiving the generated interference light and outputting a detection signal, an alignment part for performing the alignment of an optical system forming said signal light path to the eye.

DETAILED DESCRIPTION OF THE DRAWINGS

Figure 10A:
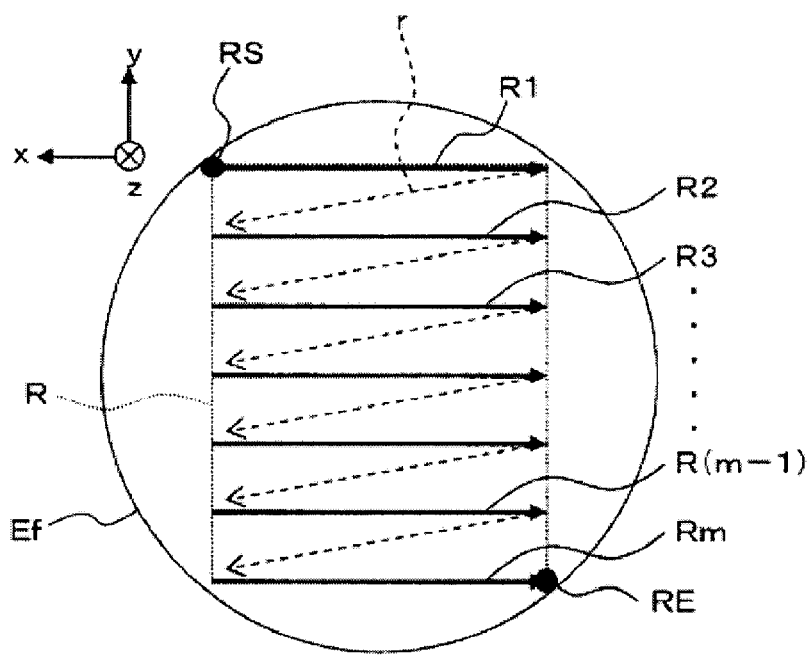
Figure 10B:
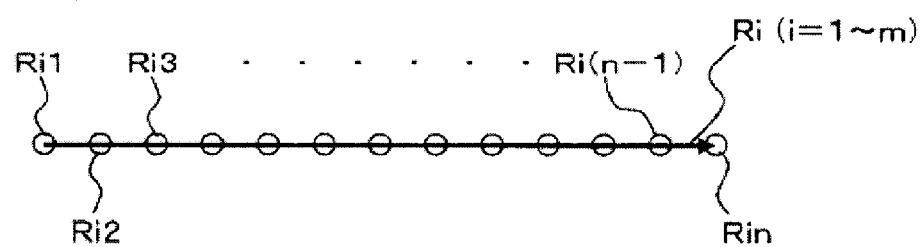

FIG. 10 is a schematic diagram representing one example of scanning features of signal light in a preferred embodiment of the ophthalmic apparatus related to the present invention. FIG. 10A represents one example of the scanning features of signal light when a fundus oculi is seen from the incident side of the signal light with respect to an eye. In addition, FIG. 10B represents one example of arrangement features of scanning points of each scanning line.

Figure 11:
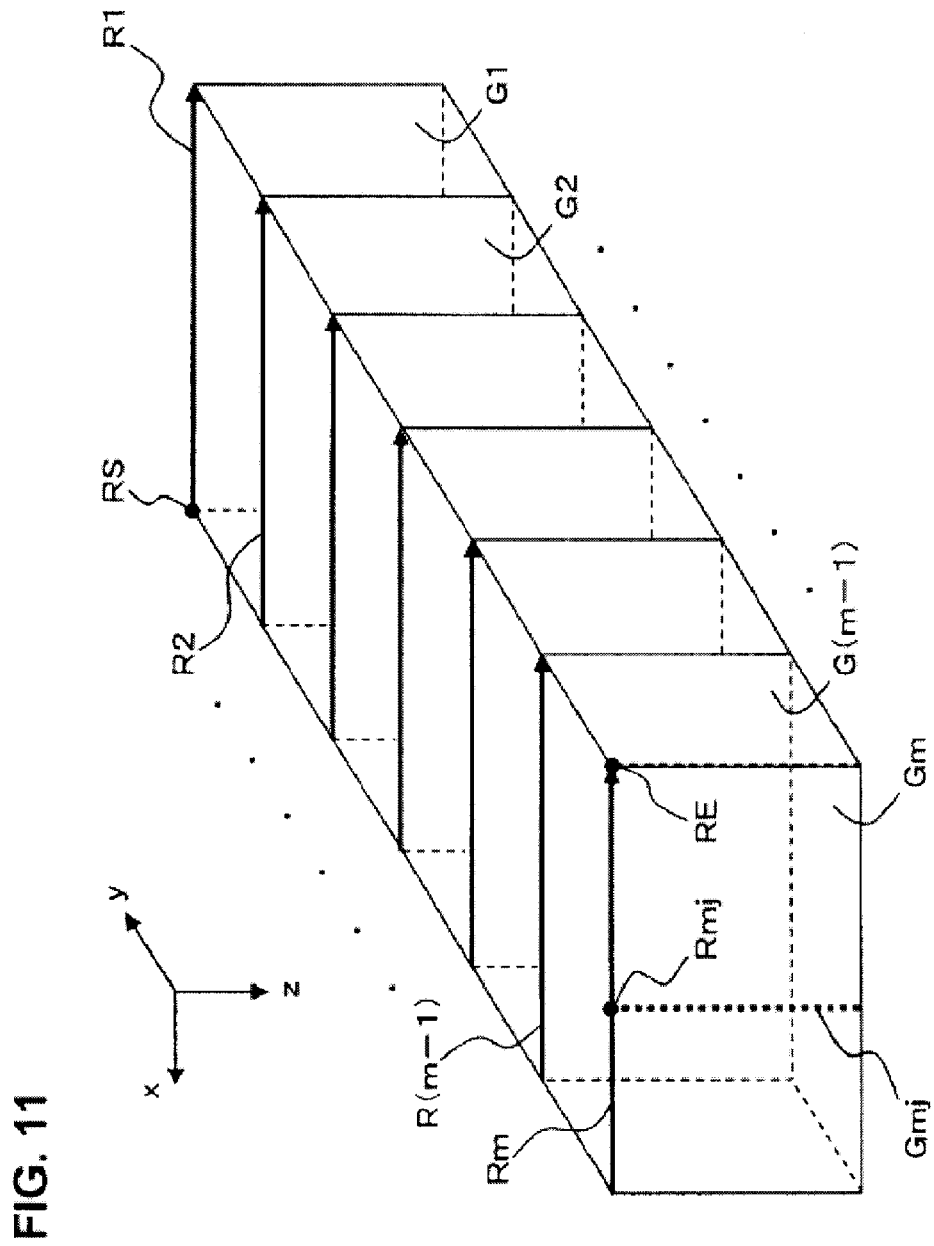

FIG. 11 is a schematic diagram representing one example of the scanning features of signal light and tomographic image features formed along each scanning line in a preferred embodiment of the ophthalmic apparatus related to the present invention.

Figure 12:
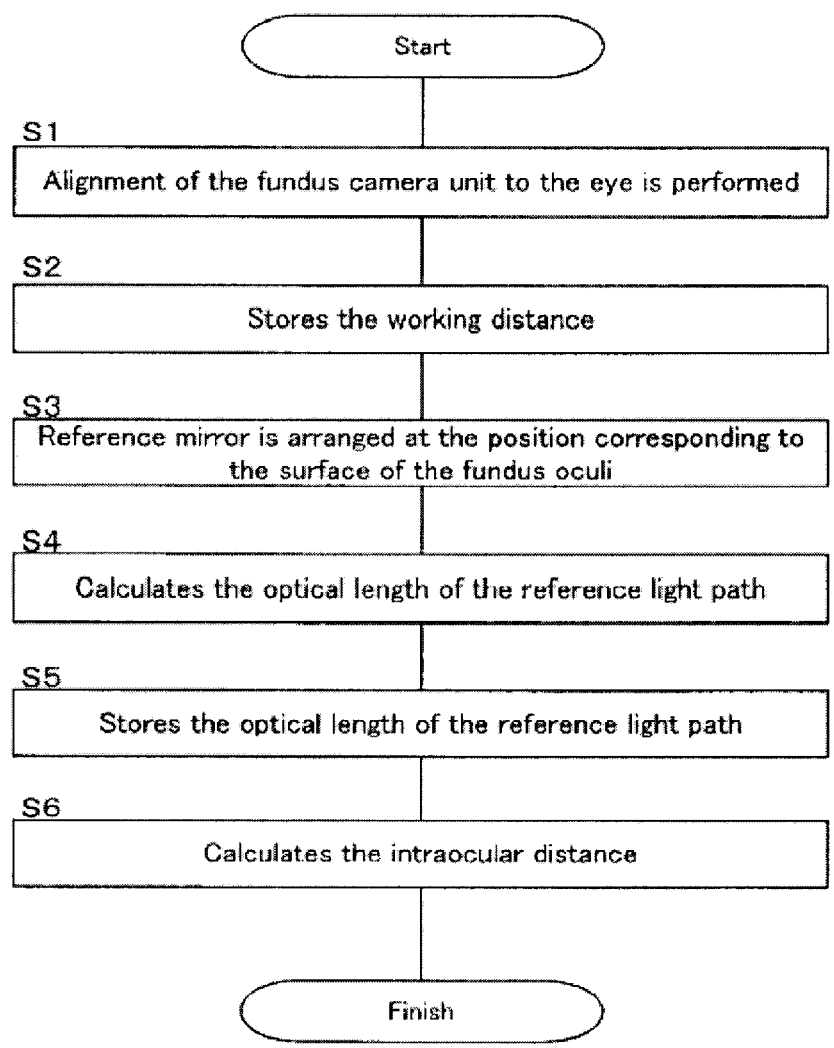

FIG. 12 is a flowchart that shows one example of the workings of preferred embodiment of an ophthalmic apparatus related to the present invention.

Figure 13:
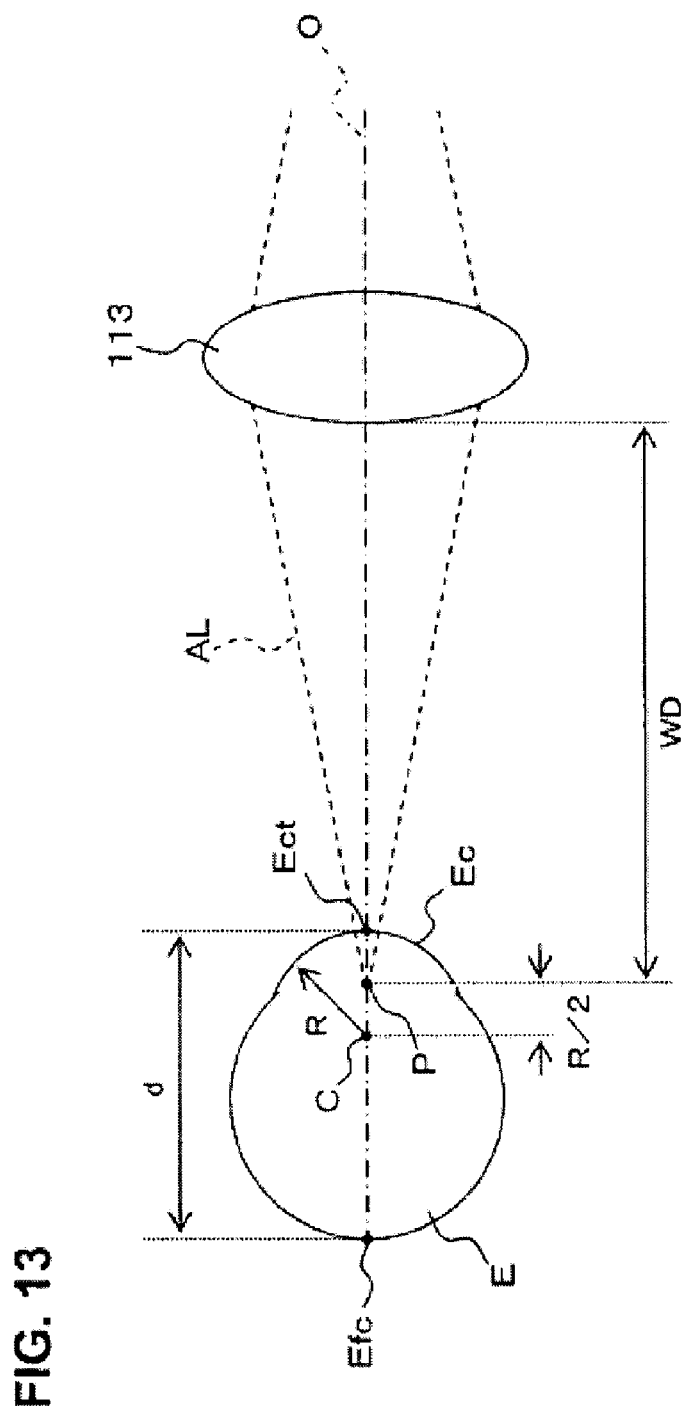

FIG. 13 is a schematic diagram showing an example of a calculation feature of intraocular distance by a modification of a preferred embodiment of the ophthalmic apparatus related to the present invention.

Figure 14:
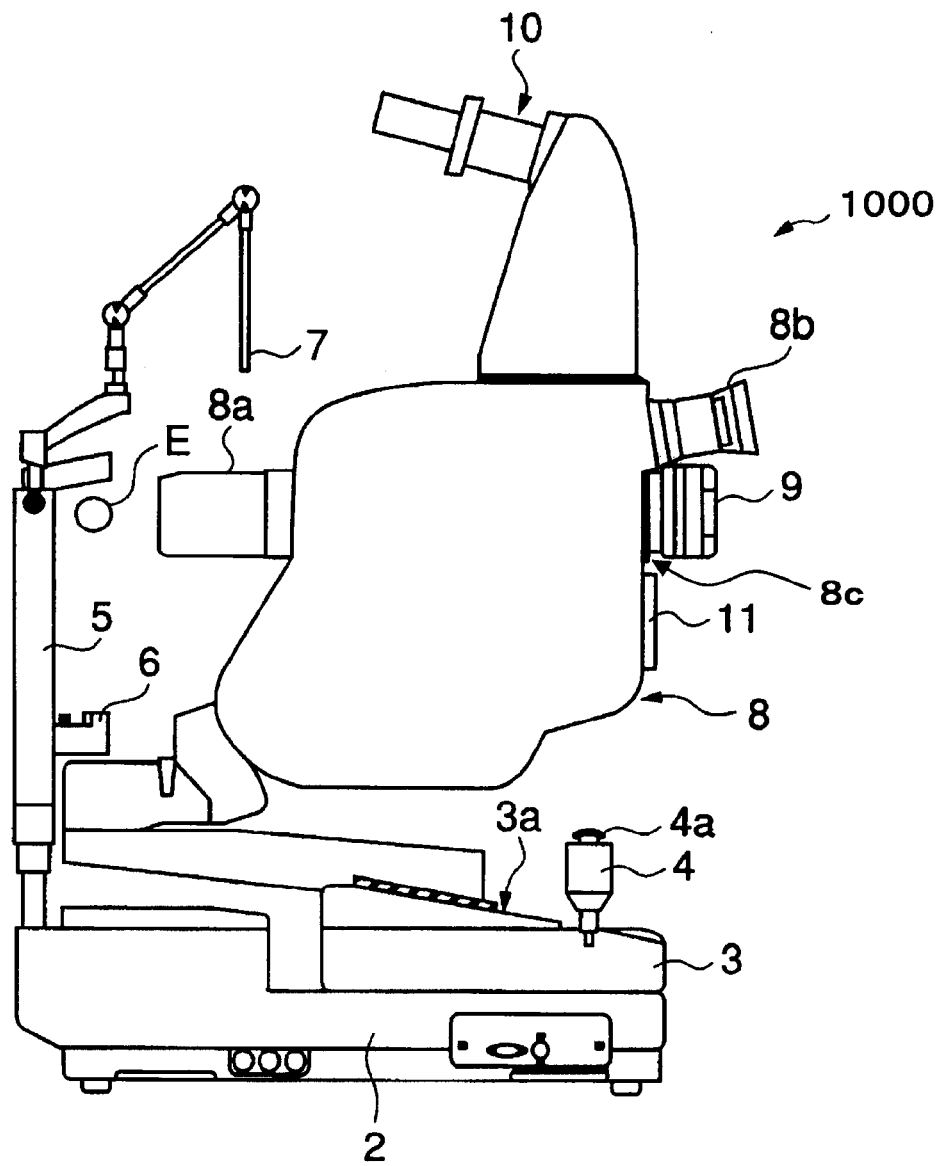

FIG. 14 is a schematic diagram showing one example of the appearance of a conventional ophthalmic apparatus (optical image measuring device).

Figure 15:
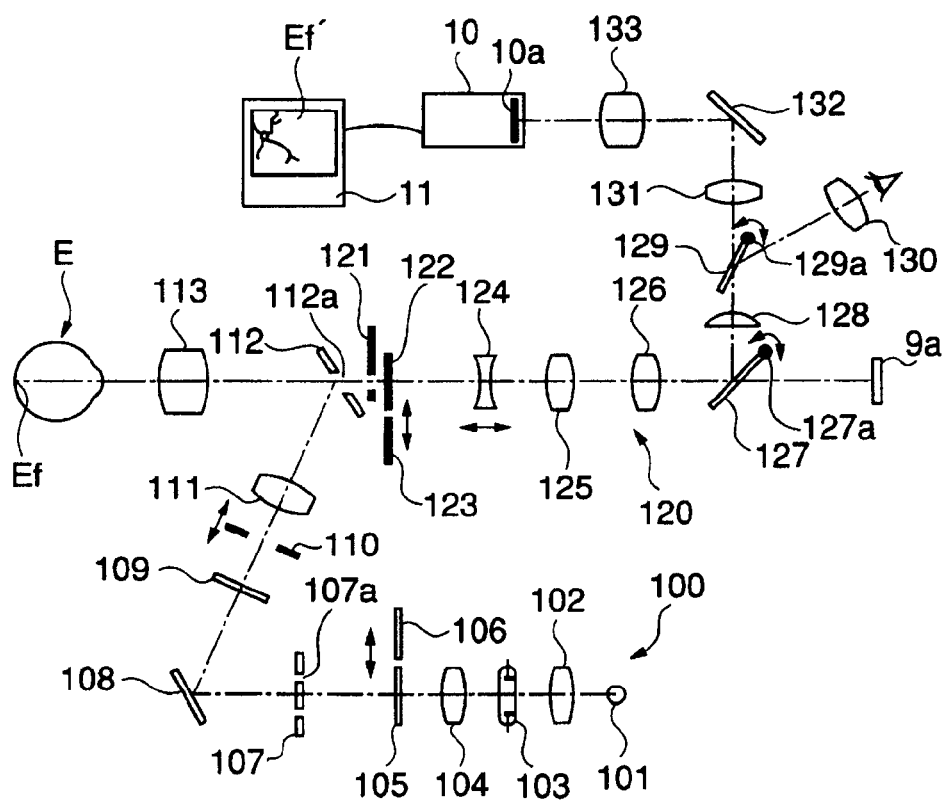

FIG. 15 is a schematic diagram representing one example of an internal configuration (an optical system configuration) of a conventional ophthalmic apparatus (fundus camera).

DETAILED DESCRIPTION OF THE PREFERRED EMBODIMENTS

One example of favorable embodiments of a ophthalmologic apparatus related to the present invention is described in detail referring to figures. Furthermore, for structural parts that are the same as conventional ones, the same symbols used in FIG. 14 and FIG. 15 are used.

Figure 1:
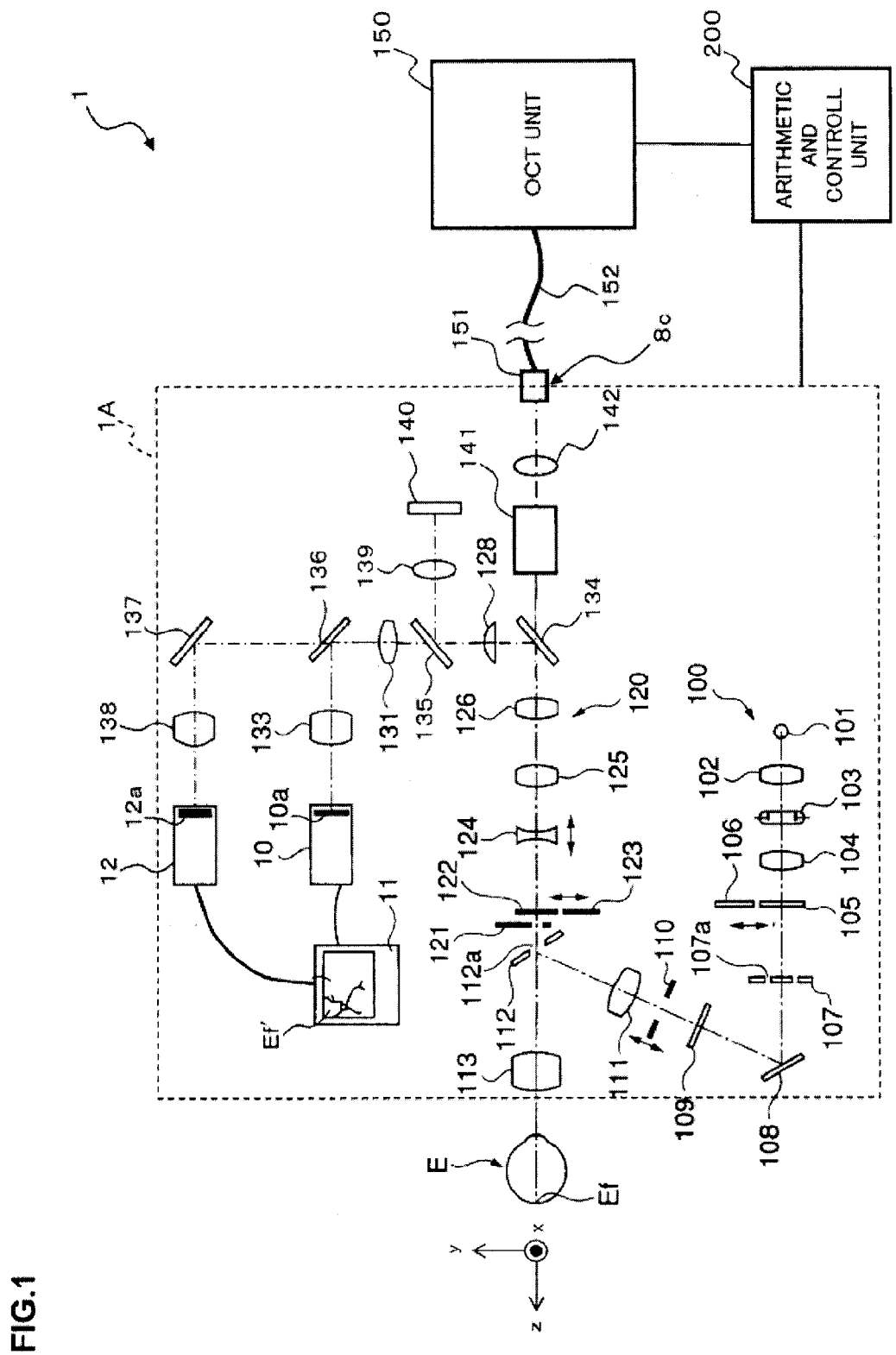
FIG. 1 is a schematic diagram representing one example of the entire configuration in a preferred embodiment of the ophthalmic apparatus related to the present invention.
Figure 3A:
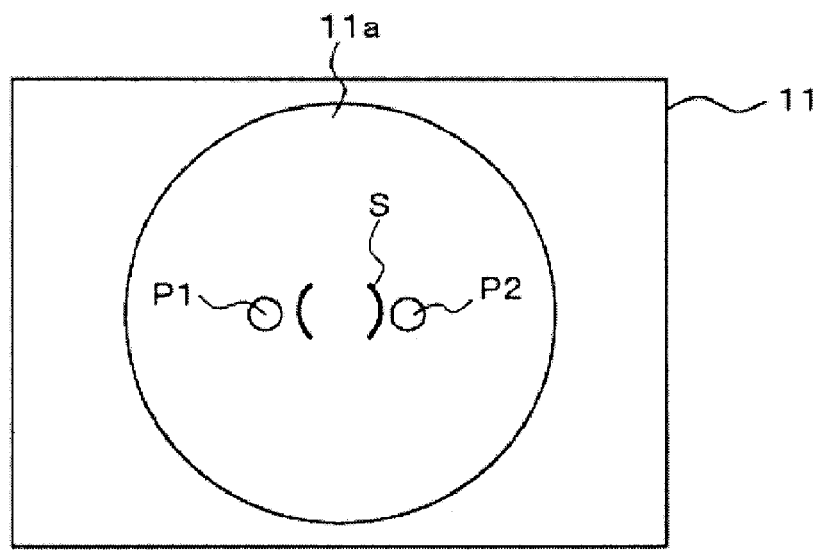
FIG. 3 is a schematic diagram representing one example of the operation of alignment using the alignment optical system in a preferred embodiment of the ophthalmic apparatus related to the present invention.
Figure 3B:
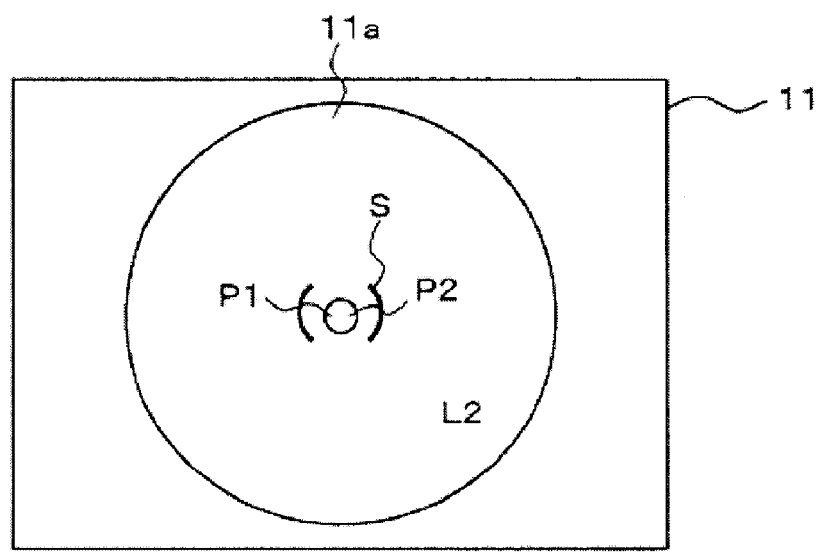
Figure 4:
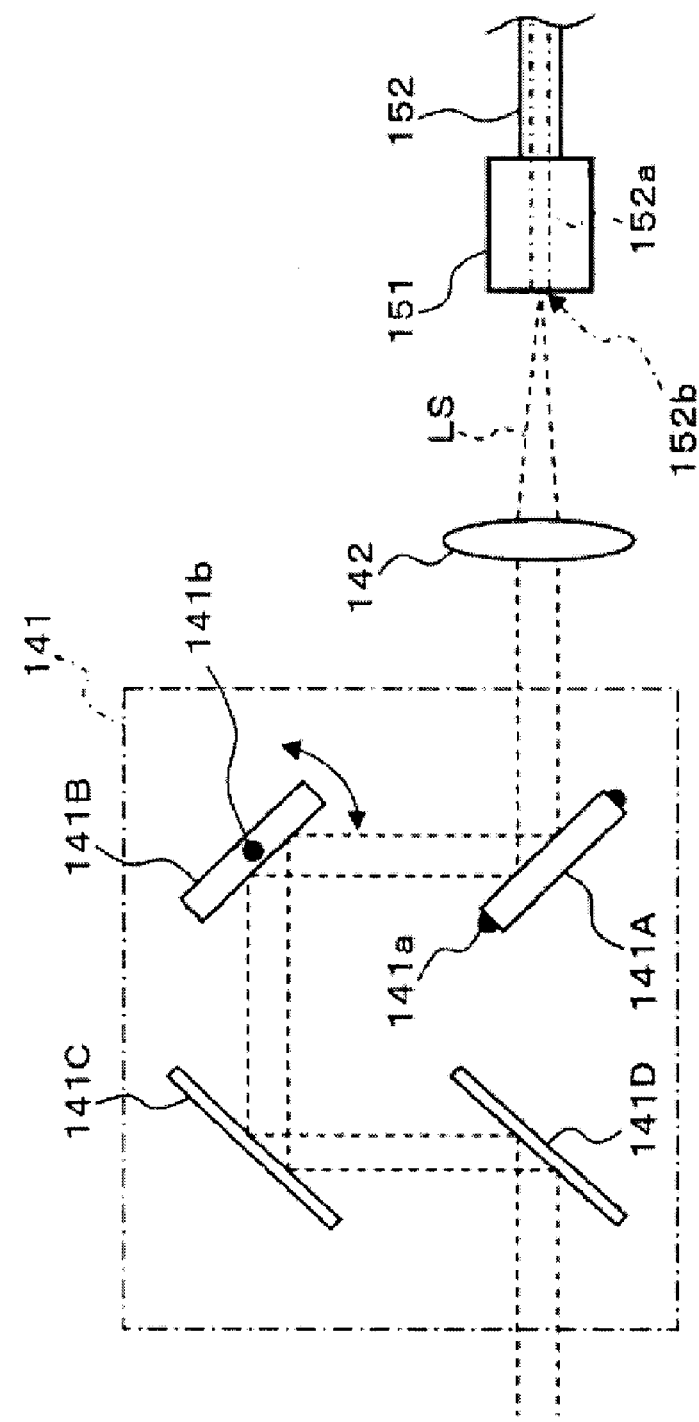
FIG. 4 is a schematic diagram representing one configured example of a scanning unit installed in a fundus camera unit in a preferred embodiment of the ophthalmic apparatus related to the present invention.
Figure 5:
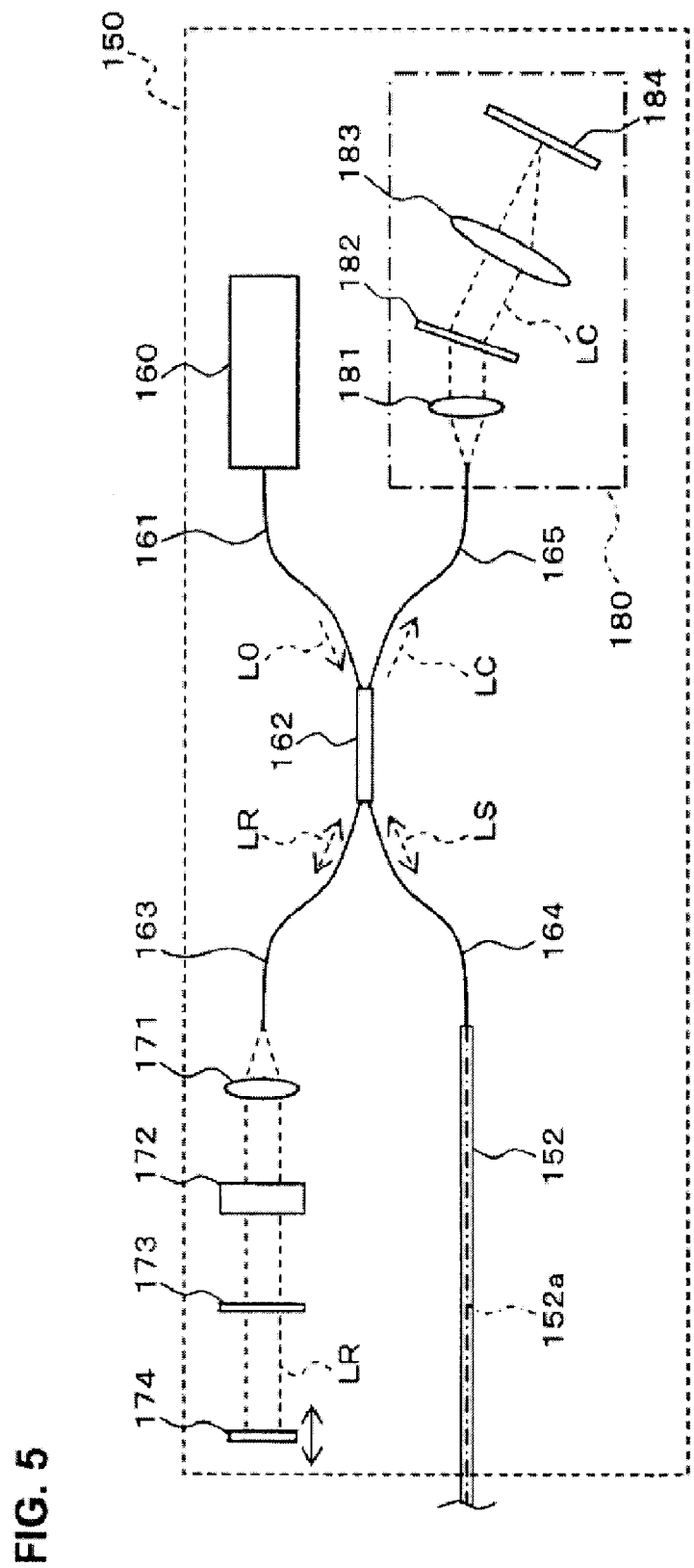
FIG. 5 is a schematic diagram representing one configured example of an OCT unit in a preferred embodiment of the ophthalmic apparatus related to the present invention.
Figure 6:
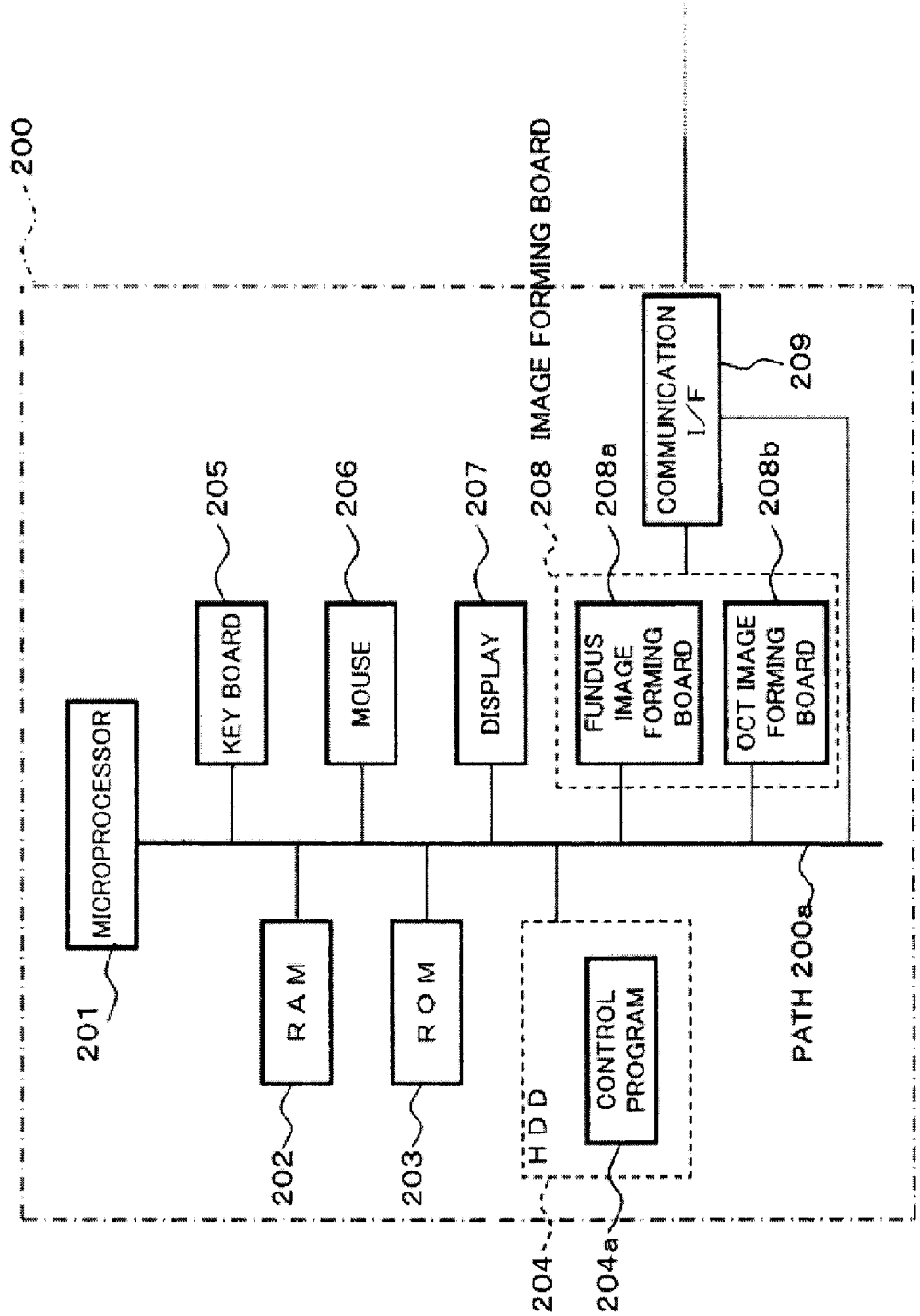
FIG. 6 is a schematic block diagram representing one example of hardware configurations of an arithmetic and control unit in an embodiment of the ophthalmic apparatus related to the present invention.
Figure 7:
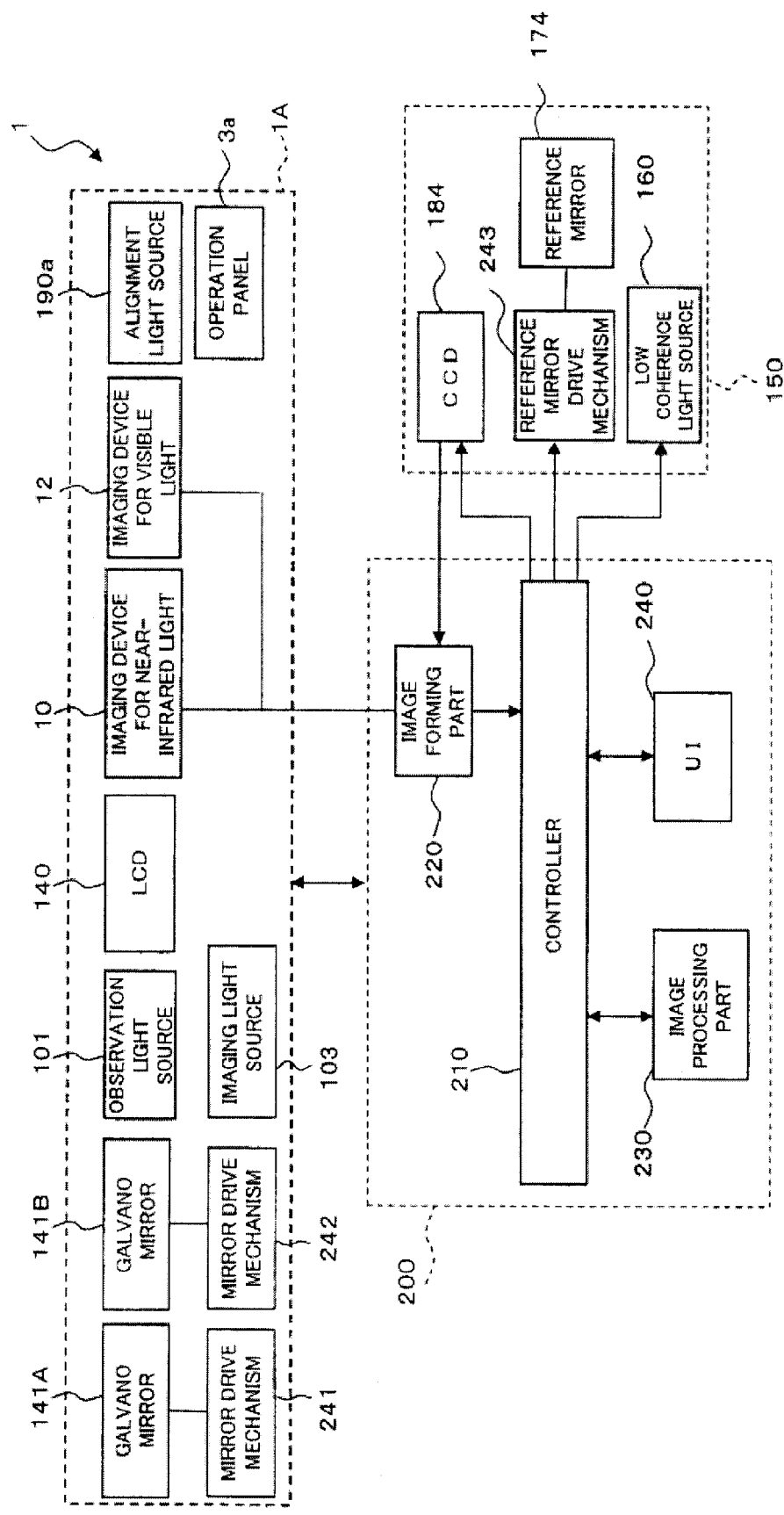
FIG. 7 is a schematic block diagram representing one configured example of a control system in a preferred embodiment of the ophthalmic apparatus related to the present invention.
Figure 8:
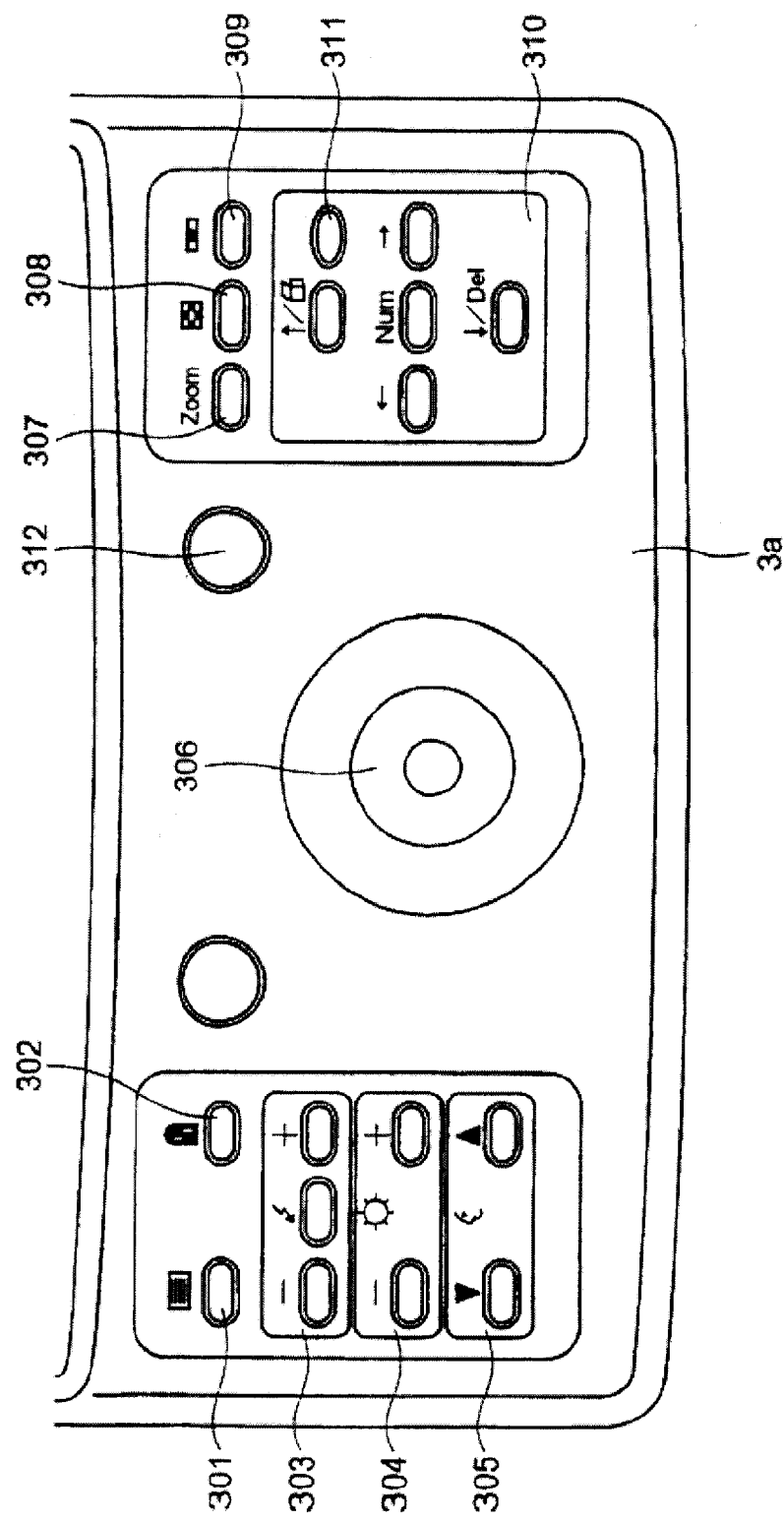
FIG. 8 is a schematic diagram showing an example of the apparent configuration of the operation panel in a preferred embodiment of the ophthalmic apparatus related to the present invention.
Figure 9:
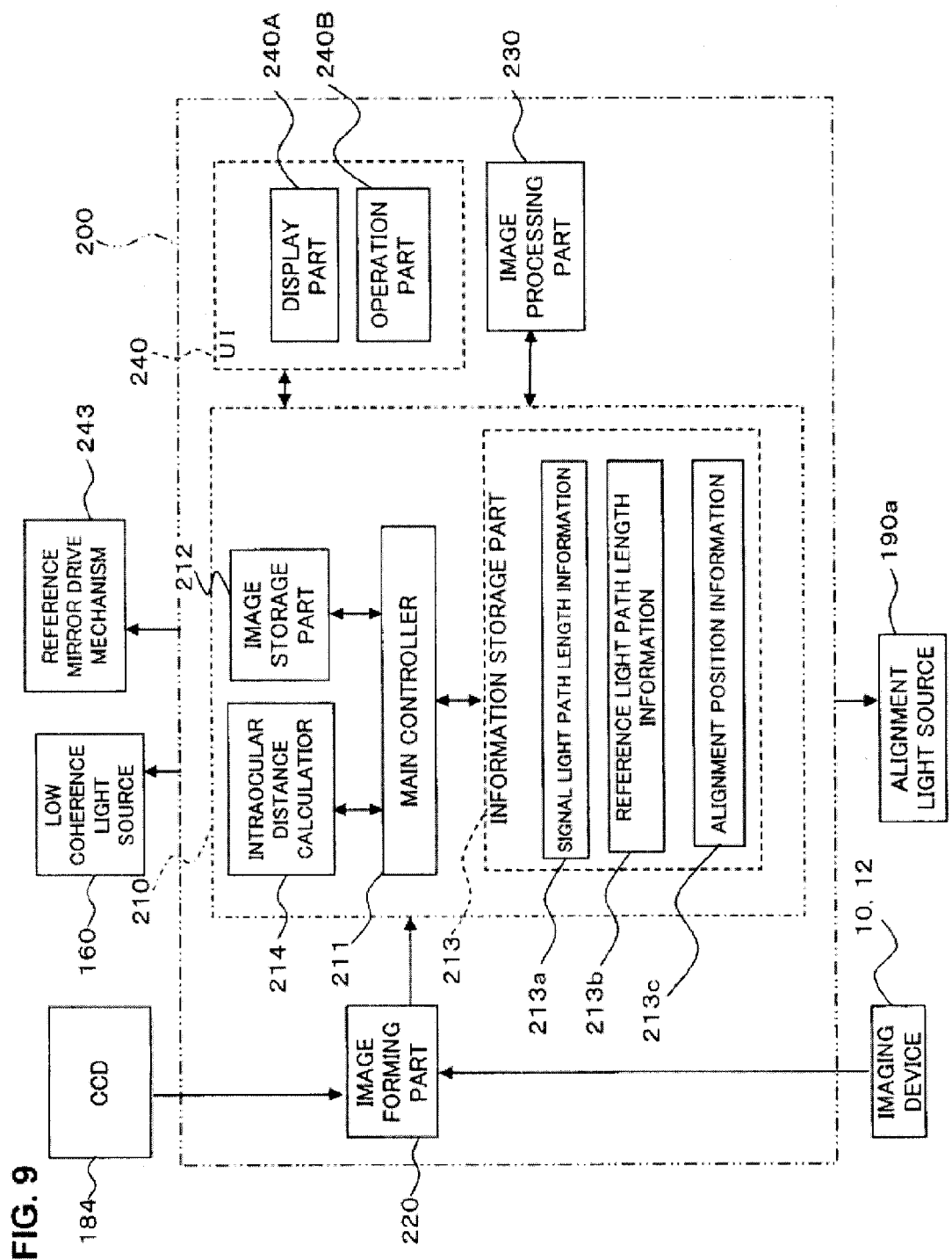
FIG. 9 is a drawing showing one example of configuration of the arithmetic and control unit in a preferred embodiment related to the present invention.

First, by referring to FIGS. 1 through 9, the configuration of the ophthalmologic apparatus related to the present invention is described. FIG. 1 shows the entire configuration of the ophthalmologic apparatus 1 related to the present invention. FIG. 2 shows the configuration of alignment optical system of the ophthalmologic apparatus 1. FIG. 3 shows the operation of alignment using the alignment optical system. FIG. 4 shows a configuration of a scanning unit 141 in a fundus camera unit 1A. FIG. 5 shows a configuration of an OCT unit 150 of the ophthalmologic apparatus 1. FIG. 6 shows a hardware configuration of an arithmetic and control unit 200 of the ophthalmologic apparatus 1. FIG. 7 shows a configuration of a control system of the ophthalmologic apparatus 1. FIG. 8 shows a configuration of an operation panel 3a provided on a fundus camera unit 1A. FIG. 9 shows a configuration of a control system of an arithmetic and control unit 200.

The Entire Configuration

As shown in FIG. 1, the ophthalmologic apparatus 1 is comprised of a fundus camera unit 1A that functions as a conventional fundus camera, an OCT unit 150 accommodating the optical system of an optical image measuring device (OCT device), and an arithmetic and control unit 200 that executes various arithmetic processes and control processes, etc.

To the OCT unit 150, one end of a connection line 152 is attached. To the other end of this connection line 152, a connector part 151 is attached. This connector part 151 is attached to a mounting part 8c shown in FIG. 14. Furthermore, a conductive optical fiber runs through the inside of the connection line 152. The OCT unit 150 and the fundus camera unit 1A are optically connected through the connection line 152. The constitution details of the OCT unit 150 are to be described later referring to FIG. 5.

Configuration of Fundus Camera Unit

First, by referring to the FIGS. 1 through 4, the configuration of fundus camera unit 1A is described. A fundus camera unit 1A is a device for forming a 2-dimensional image of the surface of a fundus oculi of an eye based on optically captured data (data detected by imaging devices 10 and 12), and the fundus camera unit 1A has substantially the same appearance as the conventional fundus camera 1000 shown in FIG. 14. Furthermore, as in the conventional optical system shown in FIG. 15, the fundus camera unit 1A is provided with an illuminating optical system 100 to light a fundus oculi Ef of an eye E, and an imaging optical system 120 for guiding the fundus reflection light of the illumination light to an imaging device 10.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with a wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an illumination diaphragm 110, a relay lens 111, an aperture mirror 112, and an objective lens 113.

The observation light source 101 emits the illumination light of a wavelength in the visible region included within about 400 nm to 700 nm. Furthermore, the imaging light source 103 emits the illumination light of a wavelength in the near-infrared region included within about 700 nm to 800 nm. The near-infrared light emitted from this imaging light source 103 is provided shorter than the wavelength of the light used by the OCT unit 150 (to be described later).

At the same time, the imaging optical system 120 comprises: an objective lens 113, an aperture mirror 112 (aperture part 112a thereof), an imaging diaphragm 121, a barrier filter 122 and 123, a focusing lens 124, a relay lens 125, an imaging lens 126, a dichroic mirror 134, a field lens 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid crystal Display) 140.

The imaging optical system 120 related to the present embodiment is different from the conventional imaging optical system 120 shown in FIG. 15 in that the dichroic mirror 134, the half mirror 135, a dichroic mirror 136, the reflection mirror 137, the imaging lens 138, and the lens 139 and LCD 140 are provided.

The dichroic mirror 134 reflects the fundus reflection light of the illumination light (with a wavelength included within about 400 nm to 800 nm) from the illuminating optical system 100, and transmits the signal light LS (with a wavelength included within about 800 nm to 900 nm; to be described later) from the OCT unit 150.

Furthermore, the dichroic mirror 136 transmits the illumination light with a wavelength in the visible region from the illuminating optical system 100 (the visible light of a wavelength within about 400 nm to 700 nm emitted from the observation light source 101) and reflects the illumination lights having a wavelength in the near-infrared region (near-infrared light of a wavelength within about 400 nm to 700 nm emitted from the observation light source 101).

The LCD 140 shows an internal fixation target, etc. The light from this LCD 140 is reflected by the half mirror 135 after being converged by the lens 139, and is reflected by the dichroic mirror 136 through the field lens 128. Further, it enters the eye E passing through the imaging lens 126, the relay lens 125, the variable focusing lens 124, the aperture mirror 112 (aperture part 112a thereof), the objective lens 113, etc. As a result, an internal fixation target, etc. is displayed in a fundus oculi Ef of an eye E.

The image pick up element 10a is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the video signal as a result of detecting near-infrared light. A touch panel monitor 11 displays a 2-dimensional image (fundus image Ef) of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 10, for example, the illumination light emitted from the imaging light source 103 of the illuminating optical system 100, having a wavelength in the near-infrared region, may be used.

Also, the image pick up element 12a is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the video signal as a result of detecting visible light. A touch panel monitor 11 displays a 2-dimensional image (fundus image Ef) of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 12, for example, the illumination light emitted from the observation light source 101 of the illuminating optical system 100, having a wavelength in the visible region, may be used.

Furthermore, the imaging optical system 120 of the present embodiment is provided with a scanning unit 141 and a lens 142. The scanning unit 141 is equipped with a configuration to scan the light (signal light LS; to be described later) emitted from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 4, one example of a concrete configuration of the scanning unit 141 is shown. The scanning unit 141 is comprised including Galvano mirrors 141A, 141B, and reflection mirrors 141C, 141D.

The Galvano mirrors 141A and 141B are to be rotatable centering around rotary shafts 141a and 141b respectively. The rotary shaft 141a and 141b are arranged perpendicular to each other. In FIG. 4, the rotary shaft 141a of the Galvano mirror 141A is arranged parallel to the paper face, while the rotary shaft 141b of the Galvano mirror 141B is arranged perpendicular to the paper face. That is, the Galvano mirror 141B is to be rotatable in the directions indicated by an arrow pointing in both directions in FIG. 4, while the Galvano mirror 141A is to be rotatable in the directions perpendicular to the arrow pointing in both directions. As a result, this pair of Galvano mirrors 141A and 141B act so that the reflecting direction of the signal light LS changes to a direction perpendicular to each other. Furthermore, the rotary movement of the Galvano mirror 141A and 141B respectively is driven by a drive mechanism (see FIG. 7) to be described later.

The signal light LS reflected by the Galvano mirrors 141A and 141B is to be reflected by reflection mirrors 141C and 141D, and is to advance in the same direction as having entered into the Galvano mirror 141A As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

A half mirror 190 is inclined on an optical path between the focusing lens 124 and the relay lens 125. The half mirror 190 acts to combine the optical path of the optical alignment system 190A shown in FIG. 2A and the optical path of the imaging optical system 120 (optical photographing path). This optical alignment system 190A represents one example of the "alignment part" of the present invention, being an optical system for projecting onto the eye E an alignment bright point to be used in the position adjustment of the optical system on the eye E.

This alignment bright point is employed for both the alignment coinciding the top of the cornea of the eye E with the optical axes of the optical systems 100 and 120 (alignment in the x-y direction shown in FIG. 1) and the alignment of the distance between the eye E and the optical systems 100 and 120 (the z direction in FIG. 1; working distance; the distance between (the top of) the cornea of the eye E and the objective lens 113) (e.g., cf. JP Patent laid-open No. Hei 11-4808).

Figure 2A:
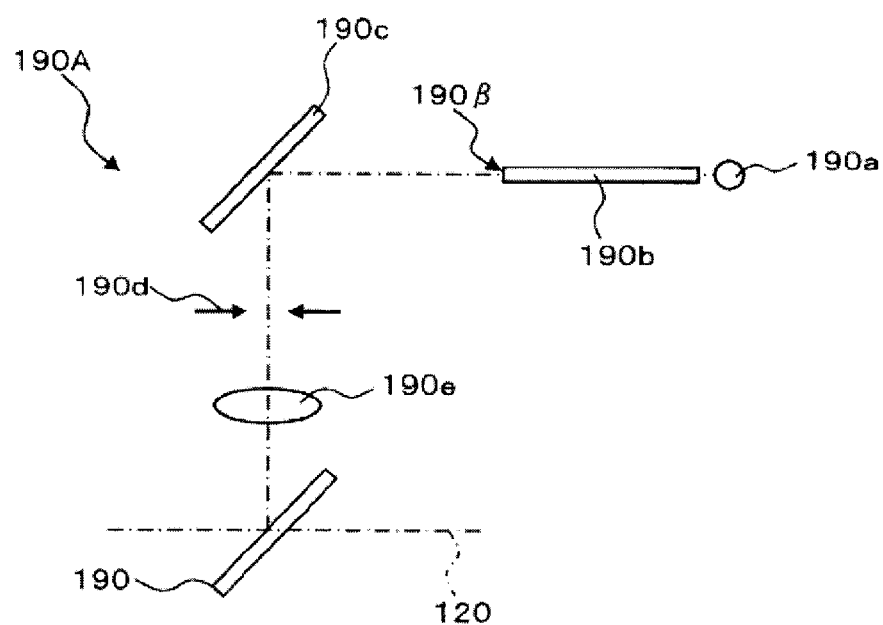
FIG. 2 is a schematic diagram representing one example of the configuration of alignment optical system of the ophthalmologic apparatus 1 in a preferred embodiment of the ophthalmic apparatus related to the present invention.

The optical alignment system 190A comprises an alignment light source 190a consisting of, for example, LED for emitting light such as a near-infrared light (alignment light), a light guide 190b, a reflection mirror 190c, a two-hole aperture 190d, and a relay lens 190e as well as the half mirror 190 as shown in FIG. 2A.

Figure 2B:
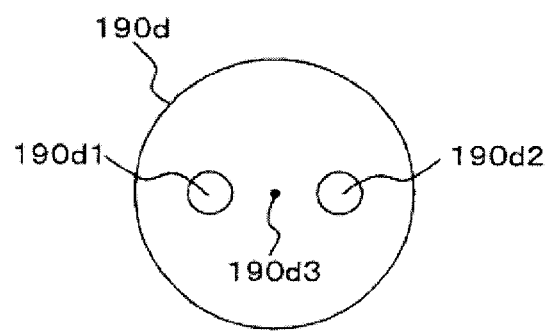

The two-hole aperture 190d has two holes 190d1 and 190d2 as shown in FIG. 2B. The holes 190d1 and 190d2 are formed at, for example, a symmetric position at the center position 190d3 of the circular two-hole aperture 190d. The two-hole aperture 190d is arranged such that the center position 190d3 is located on the optical axis of the optical alignment system 190A.

The alignment light ejected from an ejection end 190β of the light guide 190b is reflected by the reflection mirror 190c and guided to the two-hole aperture 190d. Part of the alignment light passing through the holes 190d1 and 190d2 of the two-hole aperture 190d are guided to the mirror with hole 112, passing through the relay lens 190e and being reflected by the half mirror 190. Then, the relay lens 190e makes the image of the ejection end 190β of the light guide 190b intermediately focus on the center position of the hole 112a on the mirror with hole 112 (on the optical axis of the imaging optical system 120). The alignment light that has passed through the hole 112a of the mirror with hole 112 is projected onto the cornea of the eye E via an objective lens 113.

Herein, when the positional relationship between the eye E and a fundus camera unit 1A (objective lens 113) is appropriate, that is, when the distance between the eye E and the fundus camera unit 1A (working distance) is appropriate and the optical axis of the optical system of the fundus camera unit 1A and the eye axis of the eye E (top position of the cornea) are (substantially) coincident with each other, the two light fluxes formed by the two-hole aperture 190d (alignment light fluxes) are projected onto the eye E so as to be focused on the intermediate position between the top of the cornea and the center of corneal curvature.

The corneal reflection lights of the two alignment light fluxes (alignment lights) are received by the imaging devices 10a via the imaging optical system 120. The photographed images from the imaging devices 10a are displayed on a display device such as a touch panel monitor 11 or the display of a calculation and control unit 200 (to be described later). The display feature of the alignment light at this time is shown in FIG. 3.

The symbol S in FIG. 3 indicates a scale having a bracket shape, and symbols P1 and P2 indicate the light-receiving image of the two alignment light fluxes (alignment bright point). In addition, scale S is displayed on the touch panel monitor 11 such that its center position coincides with the optical axis of the imaging optical system 120.

When the positions of the eye E and the fundus camera unit 1A are misaligned in the up-and-down direction (y direction) or the right-and-left direction (x direction), the alignment bright points P1 and P2 are displayed in positions misaligned in scale S in the up-and-down direction or the right-and-left direction as shown in FIG. 3(A). In addition, when the working distance is not appropriate, the alignment bright points P1 and P2 are each displayed at separate positions.

On the other hand, when the positions in the x-y direction of the eye E and the fundus camera unit 1A are coincident with each other and the working distance is appropriate, the alignment bright points P1 and P2 are displayed in scale S overlapping with each other as shown in FIG. 3B. An examiner performs the alignment by adjusting the positional relationship between the eye E and the fundus camera unit 1A such that the alignment bright points P1 and P2 overlap each other and are displayed in scale S.

Configuration of OCT Unit

Next, the configuration of an OCT unit 150 is described with reference to FIG. 5. The OCT unit 150 shown in the FIG. 3 is a device for forming a tomographic image of fundus oculi based on data captured by an optical scan (data detected by CCD 184 to be described below). The OCT unit 150 has a similar optical system to a conventional optical image measuring device. That is, the OCT unit 150 has an interferometer that splits the light emitted from a light source into a reference light and a signal light, and generates interference light by superposing the reference light having reached the reference object and the signal light having reached the object to be measured (fundus oculi Ef), and a device configured to output a signal as a result of detecting the interference light toward the arithmetic and control unit 200. The arithmetic and control unit 200 forms an image of the object to be measured (fundus oculi Ef) by analyzing this signal.

A low coherence light source 160 is composed of a broad band light source such as super luminescent diode (SLD) or a light emitting diode (LED), etc that emits low coherence light L0. This low coherence light L0, for instance, has a wave length in the near-infrared region and is supposed to be light having a time wise coherence length of approximately several tens of micro-meters. The low coherence light LO emitted from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 supports an example of the "light source" of the present invention.

The low coherence light L0 emitted from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. a device for splitting lights (splitter), and a device for superposing lights (coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying device for matching the optical path length (optical distance) between the reference light LR and the signal light LS, and as a device for matching the dispersion characteristics of reference light LR and the signal light LS.

Furthermore, the reference mirror 174 is provided to be movable in the propagating direction of the reference light LR. As a result, it ensures the light path length of the reference light LR according to the axial length, etc. of an eye E. Moreover, the reference mirror 174 is operated to move by a drive mechanism including a motor, etc.

Whereas, the signal light LS generated by the optical coupler 162 is guided to the end part of the connection line 152 by an optical fiber 164 consisting of such as a single mode fiber. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134 the imaging lens 126, the relay lens 125, the focusing lens 124, the imaging diaphragm 121, the aperture part 112a of an aperture mirror 112, and the objective lens 113 (then, the barrier filter 122 and 123 are retracted from the optical path respectively).

The signal light LS that has entered into the eye E forms an image on a fundus oculi (retina) Ef and is then reflected. Then, the signal light LS is not only reflected on the surface of the fundus oculi Ef, but is also scattered at the refractive index boundary reaching the deep area of the fundus oculi Ef. As a result, the signal light LS reached the fundus Ef becomes a light containing the information reflecting the surface state of the fundus oculi Ef and the information reflecting the scattered state in the rear at the refractive index boundary of the deep area tissue. The light is simply referred as fundus reflection light of the signal light LS.

The fundus reflection light of the signal light LS advances reversely on the above path and converges at the end face 152b of the optical fiber 152a, then enters into the OCT unit 150 through this optical fiber 152a, and returns to the optical coupler 162 through the optical fiber 164. The optical coupler 162 overlays this signal light LS on the reference light LR reflected at the reference mirror 174 to generate interference light LC. The generated interference light LC is guided into a spectrometer 180 through an optical fiber 165 consisting of such as a single mode fiber.

Herein, the "interference light generator" relating to the present invention is supported by an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements. This photo-detecting element supports one example of the "second detector" relating to the present invention.

The interference light LC entered the spectrometer 180 is to be resolved into spectra by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Configuration of Arithmetic and Control Unit

Next, the configuration of the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye E. The analysis technique then is the same technique as the conventional Fourier domain OCT technique.

Also, the arithmetic and control unit 200 operates to form (image data of) a 2-dimensional image showing the state of the surface of a fundus oculi Ef (retina) based on the video signal output from the imaging device 10 and 12 of the fundus camera unit 1A.

Furthermore, the arithmetic and control unit 200 executes the control of each part of the fundus camera unit 1A and the control of each part of the OCT unit 150.

As for the control of the fundus camera unit 1A, to be controlled is, for example: the emission of illumination light by the observation light source 101 or the imaging light source 103; the insertion/retraction operation of the exciter filters 105, 106, or the barrier filters 122, 123 on the optical path; the display operation of the liquid crystal display 140; the shift of the illumination diaphragm 110 (controlling the diaphragm value); the diaphragm value of the imaging diaphragm 121; the shift of the focusing lens 124; on/off operation of alignment light source; rotating operation of Galvano mirror 141A, 141B, etc.

Whereas, as for the control of the OCT unit 150, emission control of the low coherence light by a low coherence light source 160, control of accumulated time of the CCD 184, and movement control of reference mirror 174, etc. are to be performed.

The hardware configuration of the arithmetic and control unit 200 that acts as described above is explained referring to FIG. 6. The arithmetic and control unit 200 is provided with a hardware configuration that is the same as conventional computers. To be specific, the configuration includes: a microprocessor 201 (CPU,MPU, etc.), a RAM 202, a ROM 203, a hard disk drive (HDD) 204, a key board 205, a mouse 206, a display 207, an image forming board 208, and a communication interface (I/F)209. Each part of these is connected through a bus 200a.

The microprocessor 201 executes operations characteristic to the present embodiment by loading a control program 204a that has been stored in the hard disk drive 204, on the RAM 202.

Furthermore, the microprocessor 201 executes control of each part of the device that has previously been described and various arithmetic processes, etc. Moreover, control of each part of the device that responds to an operation signal from the key board 205 or the mouse 206, control of display processes by the display 207, and control of transmitting/receiving processes of various types of data or control signals, etc. are executed by the communication interface 209.

The key board 205, the mouse 206 and the display 207 are used as a user interface of the ophthalmic apparatus 1. The key board 205 is used as a device for inputting letters or figures, etc. by typing. The mouse 206 is used as a device to perform various input operations with respect to the display screen of the display 207.

Furthermore, the display 207 as an arbitrary display device such as LCD (Liquid Crystal Display) or CRT (Cathode Ray Tube), etc. displays images of a fundus oculi Ef formed by the ophthalmic apparatus 1 and displays various operation screens or set up screens, etc.

Furthermore, the user interface of the ophthalmic apparatus 1 is not limited to such a configuration but may be configured by using any user interfaces equipped with a function to display various information and a function to input various information such as track ball, control lever, touch panel type LCD, control panel for ophthalmology examinations.

An image forming board 208 is a dedicated electronic circuit for operating to form (image data of) the image of the fundus oculi Ef of an eye E. In this image forming board 208, the fundus image forming board 208a and OCT image forming board 208b are installed. The fundus image forming board 208a is a dedicated electronic circuit for operating in order to form the image of the fundus oculi based on the video signal from the imaging device 10 or the imaging device 12 of the fundus camera unit 1A. Furthermore, the OCT image forming board 208b is a dedicated electronic circuit for operating in order to form image data of tomographic images of fundus oculi Ef based on the detecting signal from CCD 184 of the spectrometer 180 in the OCT unit 150. The image forming board 208 causes the processing speed for forming image data of fundus images and tomographic images to improve.

A communication interface 209 operates to send the control signal from a microprocessor 201 to the fundus camera unit 1A and OCT unit 150. Also, the communication interface 209 operates to receive the video signal from the imaging device 10 and 12 in the fundus camera unit 1A and the detecting signal from CCD 184 in the OCT unit 150, and it operates to input the signals to the image forming board 208. At this time, the communication interface 209 operates to input the video signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Control System Configuration

The configuration of the control system of the ophthalmic apparatus 1 having the configuration described above is explained referring to FIG. 7 through FIG. 9. FIG. 7 shows a part related to the operations or processes of the present embodiment that has been particularly selected from among constituents composing the ophthalmic apparatus 1. FIG. 8 shows a configuration of an operation panel 3a provided on a fundus camera unit 1A. FIG. 9 shows a detailed configuration of the arithmetic and control unit 200.

Controller

The control system of the ophthalmic apparatus 1 is configured mainly having a controller 210 of the arithmetic and control unit 200. The controller 210 is comprised including: the microprocessor 201, the RAM 202, the ROM 203, the hard disk drive 204 (control program 204a), and the communication interface 209.

The controller 210 executes said controlling processes by the microprocessor 201 that is operated based on the control program 204a. In particular, it executes control of the mirror drive mechanism 241, 242 of the fundus camera unit 1A to independently work the Galvano mirrors 141A, 141B, control of the reference mirror drive mechanism 243 to move the reference mirror 174 toward the direction in which the reference light LR travels, and on/off operation of alignment light source.

Furthermore, the controller 210 executes control for causing the display 207 of the user interface 240 to display two kinds of images produced by the ophthalmic apparatus 1: that is, a 2-dimensional image (fundus image Ef') of the surface of a fundus oculi Ef by the fundus camera unit 1A, and an tomographic image(or sectional image, 3-dimensional image, etc.) of a fundus oculi Ef formed based on the detection signal obtained by the OCT unit 150. These images can be displayed on the display 207 both respectively and simultaneously. As to the details of configuration of the controller 210, it is described later according to FIG. 9.

Image Forming Part

An image forming part 220 is intended to operate the process forming the fundus image based on the video signal from the imaging device 10 and 12 of the fundus camera unit 1A and to operate the process forming image data of the tomographic images of fundus oculi Ef based on the detecting signal from CCD 184 in the OCT unit 150. This imaging forming part 220 comprises an imaging forming board 208. In addition, "image" may be identified with corresponding "image data" relating to the present invention.

Image Processing Part

The image processing part 230 is used for various image processes to image data of the images formed by the image forming part 220. For example, it operates to form image data of a 3-dimensional image of the fundus oculi Ef based on the tomographic images of the fundus oculi Ef corresponding to the detection signal from the OCT unit 150 and executes various corrections, such as brightness adjustment.

Herein, 3-dimensional data is image data made by assigning pixel values to each of a plurality of voxels arranged 3-dimensionally, referred to as volume data, voxel data, and so forth. When displaying an image based on volume data, the image processing part 230 operates to form image data of a pseudo 3-dimensional image seen from a particular viewing direction by applying a rendering process (such as volume rendering and MIP (Maximum Intensity Projection)) to this volume data. A display device such as a display device 207 will display such a pseudo 3-dimensional image based on the image data.

User Interface

The user interface (UI) 240, as shown in FIG. 9, comprises a display part 240A consisting of a display device such as a display 207, and an operation part 240B consisting of an operation device and an input device such as a keyboard 205 and mouse 206.

Operation Panel

The operation panel 3a of the fundus camera unit 1A is described below. This operation panel 3a is, as shown for example in FIG. 14, arranged on the platform 3 of the fundus camera unit 1A. The operation panel 3a in the present embodiment is different from the conventional configuration described above, which is provided with an operation part used to input an operation request for capturing a 2-dimensional image of the surface of the fundus oculi Ef and an operation part used for the input operation of capturing a tomographic image of the fundus oculi Ef (traditionally, only the former operation part). Consequently, the OCT can also be operated in the same manner as operation of a traditional fundus camera.

The operation panel 3a in the present embodiment is, as shown in FIG. 8, provided with a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311 and a mode switching knob 312.

The menu switch 301 is a switch operated to display a certain menu display for a user to select and specify various types of menus (such as a photographing menu for photographing a 2-dimensional image of the surface of the fundus oculi Ef and a tomographic image of the fundus oculi Ef, and a setting menu for inputting various types of settings). When this menu switch 301 is operated, the operation signal will be input to the controller 210. The controller 210 displays a menu screen on the touch panel monitor 11 or the display part 240A in response to the input of this operation signal. Incidentally, a controller (not shown) may be provided in the fundus camera unit 1A and this controller may cause the touch panel monitor 11 to display the menu screen.

The split switch 302 is a switch operated to switch the light on and off of the split bright line for focusing (e.g., see JP Patent laid-open No. H9-66031 or the like. Also referred to as split target, split mark and so on.). Incidentally, the configuration for projecting this split bright line onto an eye E to be examined (split bright line projection part) is housed, for example, in the fundus camera unit 1A (omitted in FIG. 1). When the split switch 302 is operated, the operation signal will be input to the controller 210 (or the above controller in the fundus camera unit 1A; hereinafter same as this). The controller 210 projects the split bright line onto the eye E to be examined by controlling the split bright line projection part in response to the input of this operation signal.

The imaging light amount switch 303 is a switch operated to adjust the emitted light amount of the imaging light source 103 (photographing light amount) depending on the state of the eye E to be examined (such as the degree of opacity of the lens). This imaging light amount switch 303 is provided with, for example, a photographing light amount increasing switch "+" for increasing the photographing light amount, a photographing light amount decreasing switch "−", and reset switch (button in the middle) for setting the photographing ling amount to a certain initial value (default value). When one of the imaging light amount switches 303 is operated, the operation signal will be input to the controller 210. The controller 210 adjusts the photographing light amount by controlling the imaging light source 103 depending on the operation signal that was input.

The observation light amount switch 304 is a switch operated to adjust the emitted light amount (observation light amount) of the observation light source 101. The observation light amount switch 304 is provided with, for example, an observation light amount increasing switch "+" for increasing the observation light amount and an observation light amount decreasing switch "−" for decreasing the observation light amount. When one of the observation light amount switches 304 is operated, the operation signal will be input to the controller 210. The controller 210 adjusts the observation light amount by controlling the observation light source 101 depending on the operation signal that was input.

The jaw holder switch 305 is a switch to move the position of the jaw holder 6 shown in FIG. 14. This jaw holder switch 305 is provided with, for example, an upward movement switch (upward triangle) for moving the jaw holder 6 upward and a downward movement switch (downward triangle) for moving the jaw holder 6 downward. When one of the jaw holder switches 305 is operated, the operation signal will be input to the controller 210. The controller 210 moves the jaw holder 6 upward or downward by controlling the holder movement mechanism (not shown) depending on the operation signal that was input.

The photographing switch 306 is a switch used as a trigger switch for capturing a 2-dimensional image of the surface of the fundus oculi Ef or a tomographic image of the fundus oculi Ef. When the photographing switch 306 is operated with a menu to photograph a 2-dimensional image selected, the controller 210 that has received the operation signal will control the imaging light source 103, and the display part 240A or the touch panel monitor 11. The imaging light source 103 is controlled to emit the photographing illumination light. The display part 240A or the touch panel monitor 11 is controlled to display a 2-dimensional image of the surface of the fundus oculi Ef, based on the video signal output from the imaging device 10 that has detected the fundus reflection light. On the other hand, when the photographing switch 306 is operated while a menu is selected to capture a tomographic image, the controller 210 that has received the operation signal will control the low coherence light source 160, galvanometer mirrors 141A and 141B, and display part 240A or the touch panel monitor 11. The low coherence light source 160 is controlled to emit the low coherence light LO. The galvanometer mirrors 141A and 141B are controlled to scan the signal light LS. The display part 240A or the touch panel monitor 11 is controlled to display a tomographic image of the fundus oculi Ef formed by the image forming part 220 (and image processing part 230), based on the detecting signal output from the CCD 184 that has detected the interference light LC.

The zoom switch 307 is a switch operated to change the angle of view (zoom magnification) for photographing of the fundus oculi Ef. Every time this zoom switch 307 is operated, for example, 45 degree and 22.5 degree of photographing angles of view will be set alternately. When this zoom switch 307 is operated, the controller 210 that has received the operation signal controls the focusing lens driving mechanism (not shown). The variable magnifying lens driving mechanism moves the focusing lens 124 in the optical axial direction for changing the photographing angle of view.

The image switching switch 308 is a switch operated to switch displaying images. When the image switching switch 308 is operated during a fundus oculi observation image (a 2-dimensional image of the surface of the fundus oculi Ef based on the video signal from the imaging device 12) is displayed on the display part 240A or the touch panel monitor 11, the controller 210 that has received the operation signal will control the display part 240A or the touch panel monitor 11. The display part 240A or the touch panel monitor 11 is controlled to display the tomographic image of the fundus oculi Ef. On the other hand, when the image switching switch 308 is operated during the display of a tomographic image of the fundus oculi on the display part 240A or the touch panel monitor 11, the controller 210 that has received the operation signal will control the display part 240A or the touch panel monitor 11. The display part 240A or the touch panel monitor 11 is controlled to display the fundus oculi observation image.

The fixation target switching switch 309 is a switch operated to switch the display position of the internal fixation target via the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi," "fixation position to capture the image of the peripheral region of macula lutea" and "fixation position to capture the image of the peripheral region of papilla," in a circulative fashion. The controller 210 controls the LCD 140 in response to the operation signal from the fixation target switching switch 309. The LCD 140 is then controlled to display the internal fixation target in the different positions on its display surface. Incidentally, the display positions of the internal fixation target corresponding with the above three fixation positions, for example, are preset based on clinical data or are set for each eye E to be examined (image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, an downward movement switch for moving it downward, a leftward movement switch for moving it leftward, a rightward movement switch for moving it rightward, and a reset switch for moving it to a certain initial position (default position). The controller 210, when having received the operation signal from either of these switches, will control the LCD 140. The LCD 140 is controlled to move the display position of the internal fixation target.

The fixation target size switching switch 311 is a switch operated to change the size of the internal fixation target. When this fixation target size switching switch 311 is operated, the controller 210 that has received the operation signal will control the LCD 140. The LCD 140 is controlled to change the display size of the internal fixation target. The display size of the internal fixation target can be changed, for example, between "normal size" and "enlarged size," alternately. As a result, the size of the projection image of the fixation target projected onto the fundus oculi Ef is changed.

The mode switching knob 312 is a knob rotationally operated to select various types of photographing modes (such as a fundus oculi photographing mode to photograph a 2-dimensional image of the fundus oculi, a B scan mode to perform B scan of the signal light LS, and a 3-dimensional scan mode to have the signal light LS to be scanned 3-dimensionally). In addition, this mode switching knob 312 may be capable of selecting a replay mode to replay a captured 2-dimensional image or a tomographic image of the fundus oculi Ef. In addition, it may be capable of selecting a photographing mode to control so that the photographing of the fundus oculi Ef would be performed immediately after scanning the signal light LS. Control for performing each mode is executed by the controller 210.

The controlling feature of the scanning signal light LS by the controller 210 and the process feature to the detecting signal from the OCT unit 150 by the image forming part 220 and the image processing part 230 are respectively described below. Furthermore, an explanation regarding the process of the image forming part 220, etc., to the video signal from the fundus camera unit 1A is omitted because it is the same as the conventional process.

Regarding the Signal Light Scanning

Scanning of signal light LS is performed by changing the facing direction of the reflecting surfaces of the Galvano mirrors 141A and 141B of the scanning unit 141 in the fundus camera unit 1A. By controlling the mirror drive mechanisms 241 and 242 respectively, the controller 210 changes the facing direction of the reflecting surfaces of the Galvano mirror 141A and 141B, and scans the signal light LS on the fundus oculi Ef.

Once the facing direction of the reflecting surface of the Galvano mirror 141A is changed, the signal light LS is scanned in a horizontal direction (x-direction in FIG. 1) on the fundus oculi Ef. Whereas, once the facing direction of the reflecting surface of the Galvano mirror 141B is changed, the signal light LS is scanned in a vertical direction (y-direction in FIG. 1) on the fundus oculi Ef. Furthermore, by changing the facing direction of the reflecting surfaces of both Galvano mirrors 141A and 141B simultaneously, the signal light LS may be scanned in the composed direction of x-direction and y-direction. That is, by controlling these two Galvano mirrors 141A and 141B, the signal light LS may be scanned in an arbitrary direction on the xy plane.

FIG. 10 represents one example of scanning features of signal light LS for forming images of a fundus oculi Ef. FIG. 10A represents one example of scanning features of the signal light LS, when the signal light LS sees the fundus oculi Ef from an incident direction onto the eye E (that is, + direction of z is seen from − direction of z in FIG. 1). Furthermore, FIG. 10B represents one example of arrangement features of scanning points (positions at which image measurement is carried out) on each scanning line on the fundus oculi Ef.

As shown in FIG. 10A, the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvano mirror 141A, and the scanning in a sub-scanning direction is performed by changing the facing direction of the reflecting surface of the Galvano mirror 141B.

On each scanning line Ri, as shown in FIG. 10B, plural (n number of) of scanning points Ri1 through Rin have been preset.

In order to execute the scanning shown in FIG. 10, the controller 210 controls the Galvano mirrors 141A and 141B to set the incident target of the signal light LS with respect to a fundus oculi Ef at a scan start position RS(scanning point R11) on the first scanning line R1. Subsequently, the controller 210 controls the low coherence light source 160 to flush the low coherence light L0 for emitting the signal light LS to the scan start position RS. The CCD 184 receives the interference light LC based on the fundus reflection light of this signal light LS at the scan start position RS, and outputs the detection signal to the controller 210.

Next, by controlling the Galvano mirror 141A the controller 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controller 210.

Likewise, the controller 210 obtains detection signals output from the CCD 184 responding to the interference light LC with respect to each scanning point, by flush emitting the low coherence light L0 at each scanning point while shifting the incident target of the signal light LS from scanning point R13, R14, - - - , R1 (n−1), R1n in order.

Once the measurement at the last scanning point R1n of the first scanning line R1 is finished, the controller 210 controls the Galvano mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - - , the m−1th scanning line R (m−1), the mth scanning line Rm respectively to obtain the detection signal corresponding to each scanning point. Furthermore, the symbol RE on a scanning line Rm is a scan end position in accordance with a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the emission of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvano mirror 141A and 141B is being operated, the controller 210 stores the position of each scanning line Ri or the position of each scanning point Rij (coordinates on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230.

The image forming part 220 executes the formation process of tomographic images of a fundus oculi Ef along each scanning line Ri (main scanning direction). The image processing part 230 executes the formation process of a 3-dimensional image of the fundus oculi Ef based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

FIG. 11 represents a feature of (a group of) tomographic images formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms a tomographic image Gi along this scanning line Ri. Due to the above process, m number of tomographic images (a group of tomographic images) G1 through Gm at different positions of the sub-scanning direction (y-direction) are obtained.

Next, the formation process of a 3-dimensional image of a fundus oculi Ef by the image processing part 230 is explained. A 3-dimensional image of a fundus oculi Ef is formed based on the m number of tomographic images obtained by the above arithmetic process. The image processing part 230 forms a 3-dimensional image of the fundus oculi Ef by performing a known interpolating process to interpolate an image between the adjacent tomographic images Gi and G (i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction). Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 11 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

Detailed Configuration of the Arithmetic and Control Unit

Detailed configuration of the controller of the arithmetic and control unit 200 is described with reference to FIG. 9. The controller 210 is provided with a main controller 211, an image storage part 212, an information storage part 213 and an intraocular distance calculator 214.

Main Controller

The main controller 211 comprises a microprocessor 201 or the like and controls each part of the ophthalmic apparatus 1 (previously described).

Image Storage Part

The image storage part 212 stores image data of a 2-dimensional image of the surface of the fundus oculi Ef (fundus oculi image Ef') and image data of a tomographic image of the fundus oculi Ef formed by the image forming part 220. In addition, it may be configured to store the data that forms the basis of the image data for the tomographic images. This data may be obtained by Fourier transformation of detection signals from the CCD 184 (spectral data of interference light LC) and this data represents the intensity of the signal, which corresponds to the depth of the fundus oculi Ef. Imaging the data representing the signal intensity for each depth (signal intensity data) produces the image data for the tomographic images.

A memory processing of image data to the image storage part 212 and a read processing of image data from the image storage part 212 are performed by the main controller 211. The image storage part 212 includes a memory device such as a hard disk drive 204.

Information Storage Part

The information storage part 213 stores various types of information used for the calculation processing or control processing by the calculation and control unit 200, and is constituted to include a memory device such as a hard disk drive. The information storage part 213 of the present embodiment stores signal light path length information 213a, reference light path length information 213b, and alignment position information 213c.

The signal light path length information 213a is information representing the length of the optical path of the signal light LS (signal light path). That is, it represents the length of the optical path from an optical coupler 162 of the OCT unit 150 to the objective lens 113, via an optical fiber 164, an optical fiber 152a in a connection line 152, a lens 142, a scanning unit 141, a dichroic mirror 134, an imaging lens 126, a relay lens 125, a half mirror 190, a focusing lens 124, a photographing aperture 121, and a hole 11 2a of a mirror with hole 112. The length of the optical path of the signal light LS is determined depending on the design of the optical system of the ophthalmologic apparatus 1. The signal light path length information 213a is prestored on the information storage part 213.

The reference light path length information 213b is information representing the length of the optical path of the reference light LR (reference light path). The main controller 211 moves the reference mirror 174. More specifically, the main controller 211 sends driving pulses to the reference mirror drive mechanism 243, the number of pulses depending on the desired distance of movement. The reference mirror drive mechanism 243 moves the reference mirror based on these driving pulses.

Herein, the reference mirror 174 shall be moved into a certain default position, for example, at power-on. In addition, the traveling distance of the reference mirror 174 per each one driving pulse is equal. In addition, the information storage part 213 shall prestore information on the length of the optical path of the reference light LR (default light path length information; not shown) from the optical coupler 162 to the reference mirror 174 at the default position, via an optical fiber 163, a collimator lens 171, a glass block 172, and a density filter 173.

The main controller 211 calculates the displacement of the reference mirror 174 from the aforementioned default position based on the number of driving pulses that have been sent to the reference mirror drive mechanism 243, and calculates the optical path length of the reference light LR after the reference mirror 174 has been moved based on the calculated amount of displacement and the default light path length information. The result of this calculation is stored on the information storage part 213 as reference light path length information 213*b*. This reference light path length information 213*b* is generated every time the position of the reference mirror 174 is moved.

Incidentally, it is also possible to provide a position sensor for detecting the position of the reference mirror 174 in the OCT unit 150, and to constitute the sensor so as to generate the reference light path length information 213*b* based on the detected position of the reference mirror 174.

The alignment position information 213*c* is information representing the results of alignment of the optical systems 100 and 120 in the fundus camera unit 1A to the eye E. Once the optical systems 100 and 120 are aligned at an appropriate position on the eye E, the distance between (the top of) the cornea of the eye E and the objective lens 113 (working distance) is stored on the information storage part 213 as the alignment position information 213*c*.

The working distance between the cornea of the eye E and the objective lens 113 may be always constant, or may be obtained every time alignment is performed. In the former case, the alignment position information 213*c* is always constant and prestored on the information storage part 213. In addition, in the latter case, the working distance is calculated by the controller 210, for example, based on the travel distance of a counter 3 slid on a base 2 during alignment.

Intraocular Distance Calculator

The intraocular distance calculator 214 calculates the distance between the position where the signal light LS has been introduced onto the eye E and the position where the signal light LS has been reflected by the fundus oculi Ef (intraocular distance) based on the signal light path length information 213*a*, reference light path length information 213*b*, alignment position information 213*c*, and the detection signal from the CCD 184 corresponding to the detection of the interference light LC (or signal intensity data based thereon). This intraocular distance calculator 214 represents one example of the "intraocular distance calculator" of the present invention.

The process of the intraocular distance calculator 214 will now be more specifically described. The signal light LS and the reference light LR are generated based on low coherence light LO. Therefore, the component with the greatest signal intensity among components of the interference light LC is component based on the signal light LS reflected at the position (depth) of the fundus oculi Ef corresponding to the position of the reference mirror 174.

In this embodiment, the position of the reference mirror 174 shall be set such that the certain position on the surface of the fundus oculi Ef corresponds to the position of the reference mirror 174. As a result, the component based on the signal light LS reflected by the surface of the fundus oculi Ef will have the greatest intensity among components of the signal intensity data (corresponding to the depth of the fundus oculi Ef).

As can be seen from the aforementioned discussion and FIG. 1 and FIG. 5, there is a relationship among the optical path length of the signal light path ls, the optical path length of the reference light path lr, working distance w, and the intraocular distance d from the position where the signal light LS has been introduced onto the eye E to the reflection point of the signal light LS on the fundus oculi Ef (corresponding to the position of the reference mirror 174), as follows: $lr = ls + w + d$. Therefore, the intraocular distance d can be obtained by the calculation: $d = lr - ls - w$.

The intraocular distance calculator 214, for the reflection point of the signal light LS based on the detection signal (or signal intensity data), calculates the intraocular distance d corresponding to the reflection point by assigning the optical path length ls indicated in the signal light path length information 213*a*, the optical path length lr indicated in the reference light path length information 213*b*, and the working distance w indicated in the alignment position information 213*c* to the aforementioned calculation.

Incidentally, in the alignment of the optical systems 100 and 120 of the fundus camera unit 1A to the eye E, when the optical axes of the optical systems 100 and 120 are (almost) coincident with the top of the cornea and the reflection point of the signal light LS corresponding to the position of the reference mirror 174 is (almost) coincident with the surface of the fundus oculi Ef, the intraocular distance d calculated by the intraocular distance calculator 214 is (almost) equal to the axial length of the eye E.

Operation

Operation of the ophthalmologic apparatus 1 having the above configuration will now be described. The flow chart shown in FIG. 12 shows an example of operation of the ophthalmologic apparatus 1.

First, the alignment of the optical systems 100 and 120 of the fundus camera unit 1A to the eye E is performed (S1). This alignment is performed by lighting the alignment light source 190*a* and by projecting an alignment bright point onto the eye E (described above). The main controller 211 stores the working distance determined by this alignment in the information storage part 213 as alignment position information 213*c* (S2).

Next, the reference mirror 174 is arranged at the position corresponding to the surface of the fundus oculi Ef (S3). For that purpose, for example, a tomographic image of the fundus oculi Ef is actually displayed on the display part 240A, driven by the OCT unit 150, and the position of the reference mirror 174 is adjusted such that the intensity (brightness) of the image region corresponding to the surface of the fundus oculi Ef is the greatest. In addition, the system may be configured to obtain signal intensity data, driven by the OCT unit 150, and to adjust the position of the reference mirror 174 such that the depth with the greatest intensity within the signal intensity data is coincident with the surface of the fundus oculi Ef.

The main controller 211 calculates the optical length of the reference light path corresponding to the adjusted position of the reference mirror 174 (S4), and stores the result of the calculation in the information storage part 213 as reference light path length information 213b (S5).

Then, the intraocular distance calculator 214 calculates the intraocular distance corresponding to the position of the reference mirror 174 arranged by step S3 by assigning the optical path length indicated in the signal light path length information 213a, the optical path length indicated in the reference light path length information 213b, and the working distance indicated in the alignment position information 213c to the aforementioned calculation equation (S6).

The calculated intraocular distance is stored in the information storage part 213 by the main controller 211 and displayed on the display part 240A. In addition, the system may be configured so as to send the result of the calculation to be automatically recorded on the electronic chart for that patient.

Effect and Advantage

The effect and advantage of the ophthalmologic apparatus 1 as above will be explained. This ophthalmologic apparatus 1 is an apparatus for splitting low coherence light LO into a signal light LS and a reference light LR, generating an interference light LC by having the signal light LS irradiated onto the eye E via a signal light path and reflected by the fundus oculi overlap with the reference light LR reflected by the reference mirror 174 via the reference light path, and detecting the generated light. In addition, the ophthalmologic apparatus 1 comprises a part for performing the alignment of the optical system forming the signal light path on the eye E. Then, the system functions so as to calculate the intraocular distance between the incident position of the signal light LS onto the eye E and the reflection position of the signal light LS by the surface of the fundus oculi Ef based on the length of the optical path of the signal light, the optical path of the reference light, the working distance determined by the alignment, and the results of detection of the interference light LC.

According to such ophthalmologic apparatus 1, it is possible to determine the intraocular distance on the eye E using an optical method. In addition, it is possible to arrange the reference mirror 174 into a position corresponding to the surface of the fundus oculi Ef with high accuracy by employing low coherence light; therefore, it is possible to measure the intraocular distance with high accuracy. In addition, strain is not imposed on the subject as is the case when measuring intraocular distance (such as axial length) using ultrasonic waves.

Modified Example

The configuration described above is merely one example to preferably implement the ophthalmic apparatus related to the present invention. Therefore, optional modifications may be implemented appropriately within the scope of the present invention.

In the above embodiment, the reference mirror 174 is arranged at a position corresponding to the surface of the fundus oculi Ef to determine the intraocular distance from the incident position of the signal light LS to the reflection point on the surface of fundus oculi Ef (such as axial length); however, the invention is not limited to such arrangement. For example, when arranging the reference mirror 174 at a position corresponding to a certain depth from the surface of the fundus oculi Ef, it is possible to determine the intraocular distance from the incident position of the signal light LS to the position corresponding to that certain depth by performing a process similar to that of the above embodiment.

FIG. 13 shows an example of other determining features of the intraocular distance (such as axial length) according to the ophthalmologic apparatus according to the present invention. When implementing the determining feature shown in FIG. 13, it is possible to determine the radius of curvature R (and the center of curvature C) of the cornea Ec of the eye E by setting an initial average value. In addition, the radius of curvature R may be obtained in advance, and, for example, by any apparatus capable of determining the radius of corneal curvature, such as a keratometer. Herein, the ophthalmologic apparatus of the present invention may comprise a configuration for determining the radius of curvature R. The obtained information on the radius of corneal curvature R (center of curvature C) is stored on the information storage part 213. Incidentally, the symbol O in FIG. 13 indicates the optical axes of the optical systems 100 and 120.

In the example shown in FIG. 13, when employing the optical alignment system 190A to perform the alignment of the apparatus optical system on the eye E, the alignment light (flux) AL is projected not onto the surface of the cornea Ec, but onto a position P a half of the radius of curvature R away from the center of curvature C of the cornea Ec (that is, an alignment bright point (alignment indicator) is projected onto this position P). In this case, the actual measurement of the working distance WD is obtained by measuring the distance between the front surface position of the objective lens 113 and the position P.

At this time, there is a relationship among the optical path length of the signal light path ls, the optical path length of the reference light path lr, the actual measurement of the working distance WD, and the axial length d, as follows: lr=ls+WD+d−R/2. Therefore, the axial length d can be obtained by the calculation: d=lr−ls−WD+R/2. That is, the intraocular distance calculator 214 functions to calculate the axial length d of the eye E by each subtracting the optical path length of the signal light path ls and the aligned distance (actual measured working distance) WD from the optical path length of the reference light path lr and adding the half distance of the radius of curvature R to the result of the subtraction, where the component of the signal light LS reflected by the surface of the fundus oculi Ef has the greatest intensity among the components included in the detection signal from the CCD 184.

It is possible to determine axial length with high accuracy based on the projected position of an alignment indicator by performing such axial length calculation processing.

In addition, the intraocular distance (axial length) generally includes the external axial length indicating the distance between the top of the cornea (symbol Ect in FIG. 13) and the posterior pole of eyeball (symbol Efc), and internal axial length indicating the distance between the top of the cornea (symbol Efc) and the retinal surface of the central fovea (not shown). In the ophthalmologic apparatus according to the present invention, since it is possible to obtain a tomographic image resolved in the depth-wise direction of the fundus oculi, it is possible to obtain information on the sclera for determining the external axial length, information on the retinal surface of the central fovea for determining the internal axial length, and furthermore, information on any layer of the fundus oculi (such as photoreceptor inner and outer segment and retinal pigment epithelium). As a result, the intraocular distance (axial length) can be determined based on any layer of the fundus oculi; therefore it is possible to determine intraocular distance with higher accuracy.

In order to determine the intraocular distance (axial length) on the basis of any layer or position of the fundus oculi, it is possible to provide a specifying part for specifying a layer or a position in a 2-dimensional or 3-dimensional image of the fundus oculi. As for this specifying part, for example, a pointing device such as a mouse can be employed.

As a result, it is possible to determine selectively (or concurrently) the external axial length and the internal axial length in accordance with the purpose. In addition, it is possible to determine the intraocular distance based on the desired layer or position with high accuracy. Incidentally, the position of the central fovea can be determined according to a tomographic image of the fundus oculi, so it is possible to specify a common position corresponding to the retinal surface of the central fovea for determining the external axial length or internal axial length easily and with high accuracy.

In addition, the system may also be constituted so as to detect the position of a certain layer (preset) of the fundus oculi by analyzing a tomographic image of the fundus oculi and obtain the intraocular distance (axial length) based on that layer.

Incidentally, in the example shown in FIG. 13, although alignment is performed using a virtual image obtained by the alignment light flux AL being reflected at the position half of the radius of curvature away from the center of the corneal curvature, at this time, a configuration is also possible whereby the radius of curvature R of the cornea Ec is obtained using the corneal reflection light of the alignment light flux AL from a plurality of directions sandwiching the optical axis O there between.

The ophthalmologic apparatus according to the present embodiment has a retinal camera (unit) as a device that forms two-dimensional images of the fundus oculi surface, while it may have a configuration in which a two-dimensional image of the fundus oculi surface is formed using arbitrary ophthalmological equipment such as a slit lamp biomicroscope, for example.

Moreover, in the above embodiment, the image forming process is performed by the image forming part 220 (image forming board 208) and each controlling process are operated by the controller 210 (microprocessor 201, etc.), but it can be configured to operate these two processes by one or several computers.

ADVANTAGES

The ophthalmologic apparatus related to the present invention comprises a light source for outputting a low coherence light, an interference light generating part for splitting the low coherence light output into the signal light directed toward the fundus oculi of an eye and the reference light directed toward the reference object, and overlapping the signal light irradiated onto the eye via a signal light path and reflected by the fundus oculi and the reference light reflected by said reference object via a reference light path, a detecting part for receiving the generated interference light and outputting a detection signal, an alignment part for performing the alignment of an optical system forming said signal light path to the eye, and an intraocular distance calculator for calculating the intraocular distance between the position where said signal light has been introduced and the position where said signal light has been reflected by the fundus oculi based on the optical path length of said signal light path, the optical path length of said reference light path, said aligned distance between the eye and said optical system, and said output detection signal.

With the ophthalmologic apparatus according to the present invention, it is possible to measure distance in the oculus of an eye in a different method from conventional ones.

What is claimed is:

1. An ophthalmologic apparatus comprising:
   a light source configured to emit a low coherence light;
   an interference light generator configured to split the emitted low coherence light into the signal light directed toward the fundus oculi of an eye and the reference light directed toward the reference object, and to overlap the signal light irradiated onto the eye via a signal light path and reflected by the fundus oculi and the reference light reflected by said reference object via a reference light path, so as to generate interference light;
   a detector configured to receive the generated interference light and to output a detection signal;
   an alignment part configured to align an optical system forming said signal light path to the eye; and
   an intraocular distance calculator operable to determine the intraocular distance based on the optical path length of said signal light path, the optical path length of said reference light path, said aligned distance between the eye and said optical system, and said output detection signal, the intraocular distance being between the incident position of said signal light onto the eye and the reflection position of said signal light at the fundus oculi.

2. An ophthalmologic apparatus according to claim 1, wherein said intraocular distance calculator determines said intraocular distance by subtracting the optical length of said signal light path and said aligned distance from the optical path of the reference light path, where intensity of the corresponding component of the portion of said signal light reflected by the surface of the fundus oculi is the greatest among the portions included in said detection signal.

3. An ophthalmologic apparatus according to claim 2, wherein:
   the incident position of said signal light is a position at the top of the cornea of the eye, and
   said intraocular distance calculator determines the axial length between the position at the top of the cornea and the center position on the surface of the fundus oculi.

4. An ophthalmologic apparatus according to claim 1, wherein:
   said alignment part projects an alignment indicator onto the position half of the radius of curvature away from the center of the corneal curvature,
   said aligned distance is the distance between the projection points of said alignment indicator and said optical system, and
   said intraocular distance calculator determines the axial length of the eye by subtracting the optical length of said signal light path and said aligned distance from the optical path of the reference light path and adding half of the distance of said radius of curvature to the results of the subtraction, where the intensity of the corresponding component of portion of said signal light reflected by the surface of the fundus oculi is the greatest among the portions included in said detection signal.

* * * * *

UNITED STATES PATENT AND TRADEMARK OFFICE
CERTIFICATE OF CORRECTION

| | | |
|---|---|---|
| PATENT NO. | : 7,370,966 B2 | Page 1 of 1 |
| APPLICATION NO. | : 11/697042 | |
| DATED | : May 13, 2008 | |
| INVENTOR(S) | : Yasufumi Fukuma, Hiroyuki Otsuka and Kazuhiko Yumikake | |

It is certified that error appears in the above-identified patent and that said Letters Patent is hereby corrected as shown below:

Title Page and Col. 1
The title "Opthalmologic apparatus" it should change to --Ophthalmologic apparatus--

Signed and Sealed this

Fifteenth Day of July, 2008

JON W. DUDAS
*Director of the United States Patent and Trademark Office*